(12) United States Patent
Swan et al.

(10) Patent No.: US 11,369,298 B2
(45) Date of Patent: Jun. 28, 2022

(54) SYSTEM AND A METHOD FOR MEASUREMENT OF MOMENTARY URINE FLOW AND URINE VOLUME, AND THE ANALYSIS OF URINE FLOW PROPERTIES

(71) Applicant: KESEM HEALTH PTY LTD, Oakleigh South (AU)

(72) Inventors: Matthew Swan, Box Hill (AU); Gil Hidas, Oakleigh South (AU); Andrew C. Jenkins, Box Hill (AU)

(73) Assignee: KESEM HEALTH PTY LTD, Oakleigh South (AU)

( * ) Notice: Subject to any disclaimer, the term of this patent is extended or adjusted under 35 U.S.C. 154(b) by 640 days.

(21) Appl. No.: 16/332,914

(22) PCT Filed: Sep. 13, 2017

(86) PCT No.: PCT/IB2017/055527
§ 371 (c)(1),
(2) Date: Mar. 13, 2019

(87) PCT Pub. No.: WO2018/051244
PCT Pub. Date: Mar. 22, 2018

(65) Prior Publication Data
US 2019/0231244 A1    Aug. 1, 2019

Related U.S. Application Data

(60) Provisional application No. 62/393,775, filed on Sep. 13, 2016.

(51) Int. Cl.
*A61B 5/00*      (2006.01)
*A61B 5/20*      (2006.01)
(Continued)

(52) U.S. Cl.
CPC ............. *A61B 5/208* (2013.01); *A61B 5/202* (2013.01); *E03D 11/02* (2013.01); *G01F 1/06* (2013.01)

(58) Field of Classification Search
CPC ......... A61B 5/208; A61B 5/202; E03D 11/02; G01F 1/06
(Continued)

(56) References Cited

U.S. PATENT DOCUMENTS 3,241,368 A * 3/1966 Newitt ............... G01F 23/2966
                                                      73/290 B
3,642,171 A * 2/1972 Ernst ........................ G01F 1/06
                                                      222/59
(Continued)

FOREIGN PATENT DOCUMENTS

DE         3007855 A1     9/1981
JP         09220216 A     8/1997
(Continued)

*Primary Examiner* — May A Abouelela
(74) *Attorney, Agent, or Firm* — Browdy and Neimark, P.L.L.C.

(57) ABSTRACT

An apparatus for measuring the flow rate of urine, including an encasement, configured to encase components of the apparatus; a receptacle bowl attached to the encasement, configured to be placed over a toilet bowl or seat, and direct fluid through a single point of exit to a fluid flow guide; the fluid flow guide, configured to transfer fluid from the receptacle bowl to an impeller; the impeller, configured to rotate along a rotation axis, wherein the impeller includes a plurality of blades, configured to receive the urine from the flow guide, and thereby rotate the impeller at a speed correlating with the flow rate of the urine; and an angular velocity sensor, configured to produce electric signals that correlate with the angular velocity or angular position of the impeller.

15 Claims, 22 Drawing Sheets

(51) Int. Cl.
*E03D 11/02* (2006.01)
*G01F 1/06* (2006.01)

(58) Field of Classification Search
USPC .................................................. 600/573, 576
See application file for complete search history.

(56) References Cited

U.S. PATENT DOCUMENTS

| | | | | |
|---|---|---|---|---|
| 3,919,455 A * | 11/1975 | Sigdell | ................. | G01F 23/242 73/226 |
| 4,100,802 A * | 7/1978 | Layton | ................. | A61B 5/208 600/584 |
| 4,137,573 A * | 2/1979 | Kroeger | ............... | A61B 10/007 248/214 |
| 4,187,722 A * | 2/1980 | Layton | ................. | A61B 5/208 600/584 |
| 4,200,112 A * | 4/1980 | McWhorter | ........... | A61B 5/208 600/574 |
| 4,203,169 A * | 5/1980 | Dale | ................... | A61B 10/007 4/144.1 |
| 4,241,017 A * | 12/1980 | Balistreri | ............... | A61B 5/208 4/144.1 |
| RE30,607 E * | 5/1981 | Manschot | ................ | A61B 5/20 600/575 |
| 4,287,775 A * | 9/1981 | Hutton | ..................... | G01F 1/06 600/539 |
| 4,301,813 A * | 11/1981 | Merry | ................... | A61F 5/4404 600/575 |
| 4,343,316 A * | 8/1982 | Jespersen | ............... | A61B 5/201 600/575 |
| 4,554,687 A * | 11/1985 | Carter | ...................... | G01F 1/52 4/144.1 |
| 4,589,280 A * | 5/1986 | Carter | ................... | A61B 5/201 600/573 |
| 4,590,805 A * | 5/1986 | Baird | ....................... | G01F 1/06 73/861.77 |
| 4,599,892 A * | 7/1986 | Doshi | ................... | G01F 23/296 73/149 |
| 4,656,873 A * | 4/1987 | Stewart | .................... | G01F 1/06 73/861.33 |
| 4,658,834 A * | 4/1987 | Blankenship | .......... | A61B 5/208 600/584 |
| 4,683,748 A * | 8/1987 | Carter | ................... | A61B 5/201 600/573 |
| 4,753,249 A * | 6/1988 | Muller | .................. | A61B 5/208 600/573 |
| 4,793,190 A * | 12/1988 | Chang | ...................... | G01F 1/06 116/274 |
| 4,860,767 A * | 8/1989 | Maekawa | ............... | E03D 11/00 600/573 |
| 4,901,736 A * | 2/1990 | Huang | .................... | E03D 11/02 600/573 |
| 4,962,550 A * | 10/1990 | Ikenaga | ............... | A61B 10/007 4/314 |
| 4,982,741 A * | 1/1991 | Saito | ..................... | G01N 33/493 600/584 |
| 5,062,304 A * | 11/1991 | Van Buskirk | ......... | G01F 23/263 73/861 |
| 5,119,675 A * | 6/1992 | Mohiuddin | .............. | A61B 5/20 600/580 |
| 5,263,370 A * | 11/1993 | Murata | ................... | A61B 5/208 600/584 |
| 5,487,393 A * | 1/1996 | Haswell | ............... | A61B 10/007 600/549 |
| 5,638,174 A * | 6/1997 | Henderson | ................ | G01F 1/06 356/338 |
| 5,823,972 A * | 10/1998 | McRae | ................... | A61B 5/205 600/573 |
| 6,079,280 A | 6/2000 | Miller et al. | | |
| 6,212,698 B1 * | 4/2001 | Stingley | ............... | A61B 10/007 4/144.1 |
| 6,358,477 B1 * | 3/2002 | Webb | ................... | A61B 10/007 4/144.1 |
| 6,582,379 B1 | 6/2003 | Stisen | | |
| 6,640,649 B1 * | 11/2003 | Paz | ...................... | A61M 5/1689 73/861.41 |
| 7,416,542 B2 * | 8/2008 | Aundal | ................... | A61B 5/208 600/419 |
| 7,607,362 B1 * | 10/2009 | Brost | ........................ | G01F 1/06 73/202 |
| 8,337,476 B2 * | 12/2012 | Greenwald | ............. | G01F 1/662 604/318 |
| 9,155,525 B2 * | 10/2015 | Lipinsky | ............... | A61B 10/007 |
| 9,592,034 B2 * | 3/2017 | Hall | ............................ | E03D 9/00 |
| 10,030,782 B2 * | 7/2018 | Cochart | ................... | E03D 3/06 |
| 10,130,293 B2 * | 11/2018 | Hidas | ................... | A61B 5/0022 |
| 10,182,747 B2 * | 1/2019 | Charlez | ................ | A61B 5/208 |
| 10,219,733 B2 * | 3/2019 | Shimokawa | ........... | G01F 1/075 |
| 10,238,314 B2 * | 3/2019 | Connolly | .............. | A61B 5/7465 |
| 2004/0243074 A1 * | 12/2004 | Mulder | ................... | A61B 5/208 604/318 |
| 2005/0256428 A1 | 11/2005 | Aundal | | |
| 2006/0184064 A1 * | 8/2006 | Paasch | ................. | A61B 10/007 600/573 |
| 2008/0312550 A1 * | 12/2008 | Nishtala | ................. | A61B 5/208 600/549 |
| 2009/0287170 A1 * | 11/2009 | Otto | ........................ | A61B 5/208 604/318 |
| 2011/0265576 A1 * | 11/2011 | Cha | .......................... | G01F 1/007 73/700 |
| 2015/0342574 A1 * | 12/2015 | Hall | ....................... | A61B 5/208 600/573 |
| 2016/0183803 A1 * | 6/2016 | Mosli | ................... | A61B 5/1128 600/476 |
| 2017/0013562 A1 | 1/2017 | Lim et al. | | |
| 2017/0059384 A1 * | 3/2017 | Della-Monica | ..... | G01F 15/0755 |
| 2017/0135622 A1 * | 5/2017 | Shimokawa | ........... | A61B 5/208 |
| 2017/0138772 A1 * | 5/2017 | Neilson | ..................... | F01D 5/02 |
| 2018/0064424 A1 * | 3/2018 | Ulusahin | ................ | G01F 9/003 |

FOREIGN PATENT DOCUMENTS

| | | |
|---|---|---|
| JP | 09248289 A | 9/1997 |
| WO | 2000065313 A1 | 11/2000 |
| WO | 2009143113 A1 | 11/2009 |

\* cited by examiner

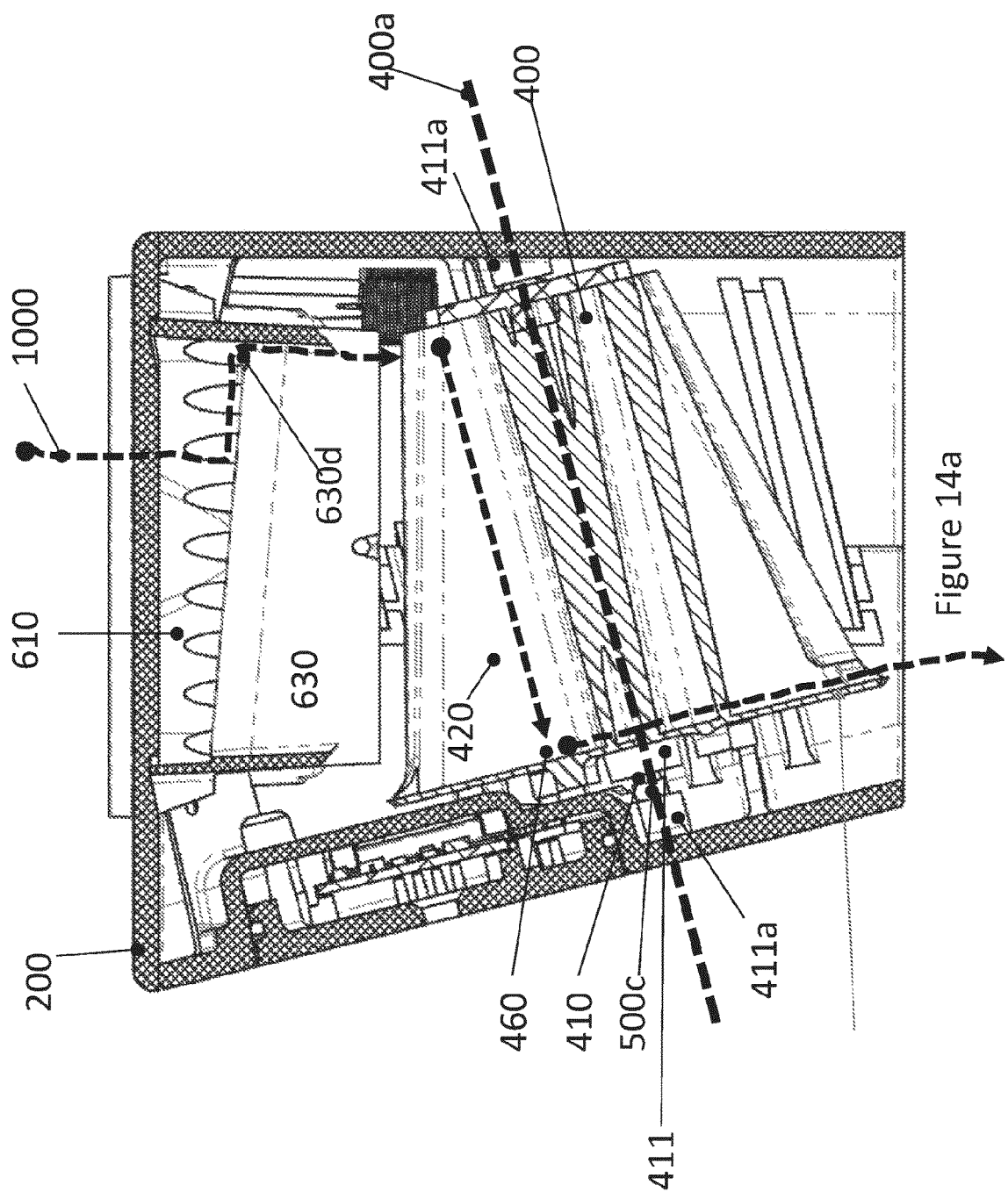

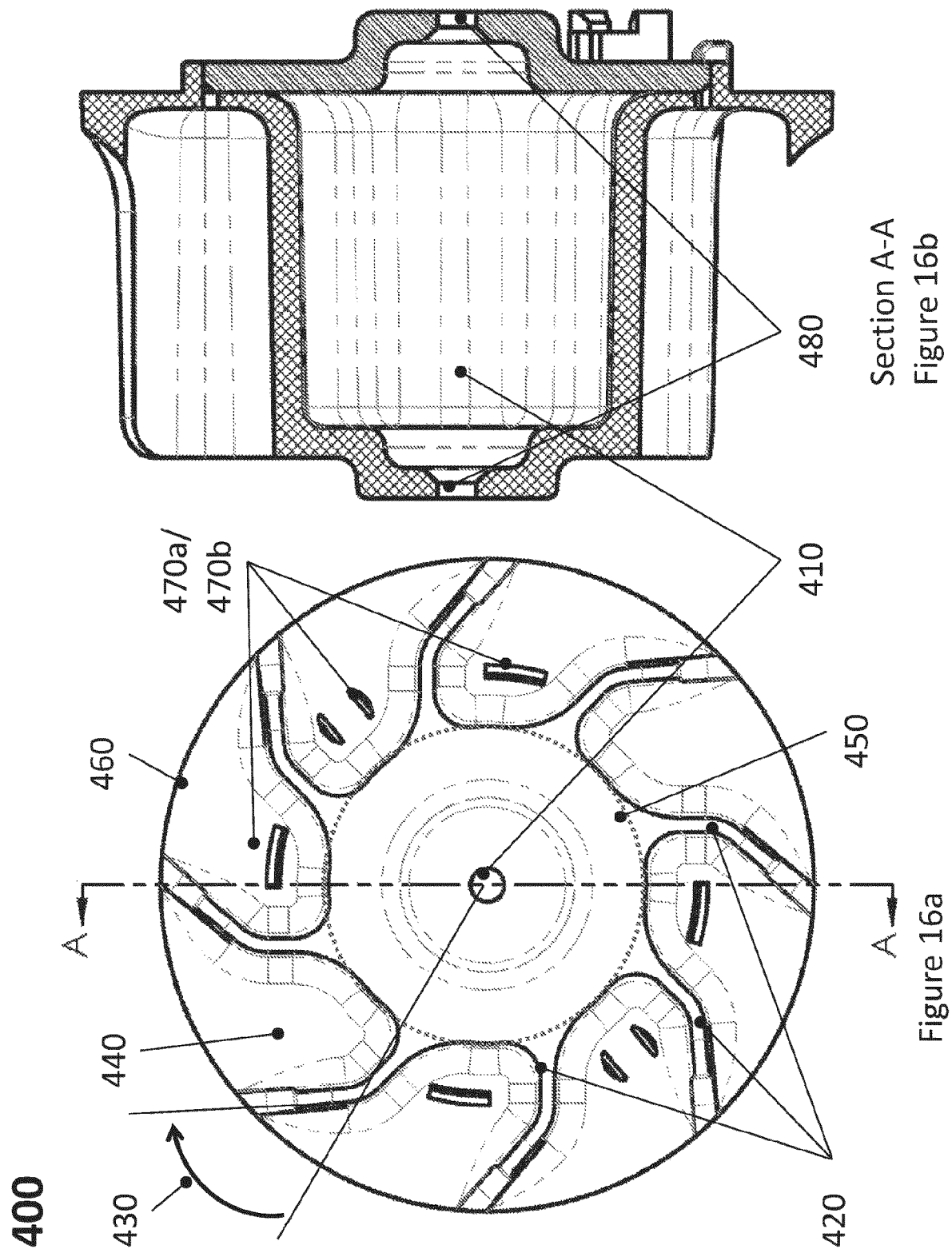

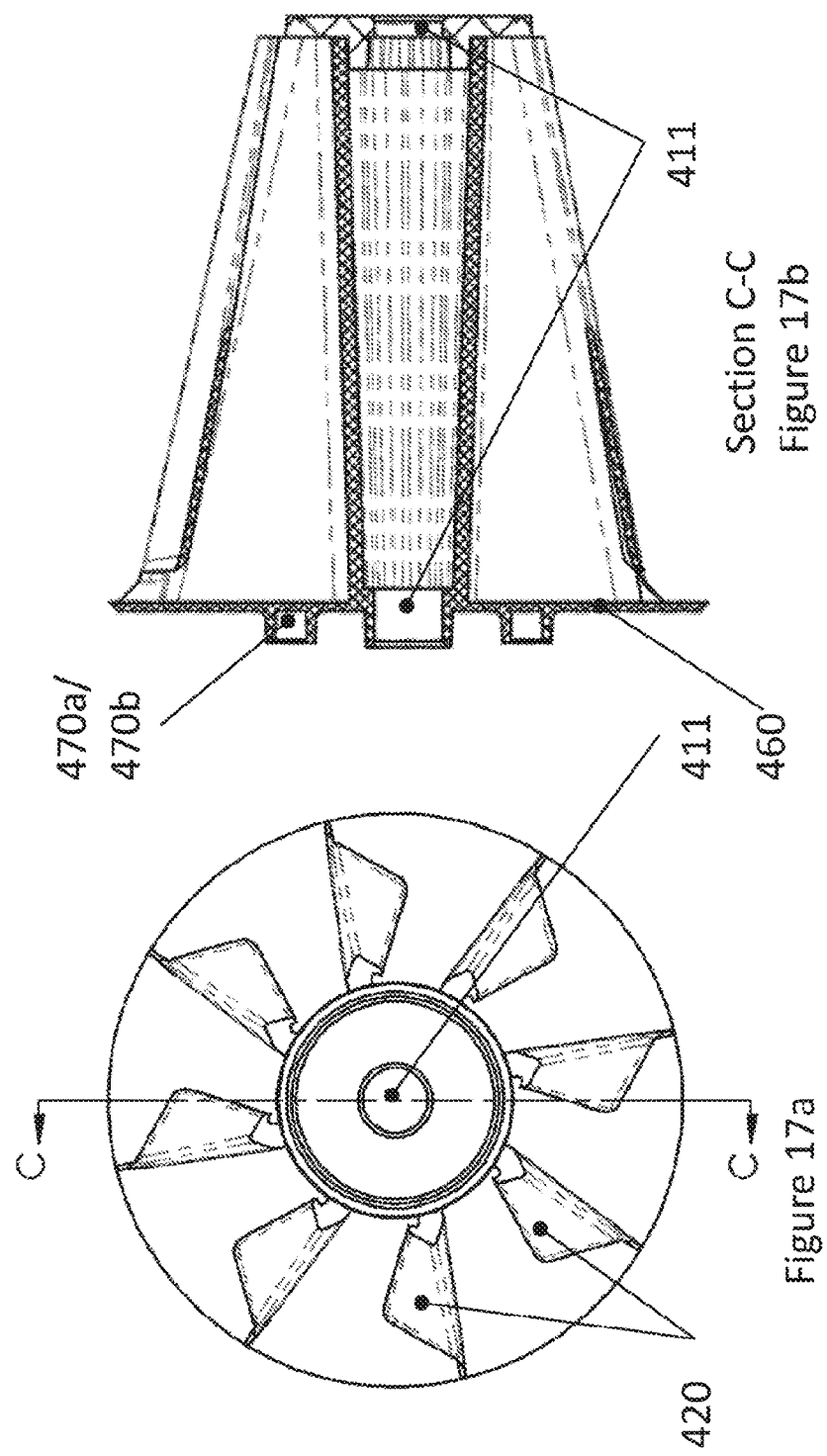

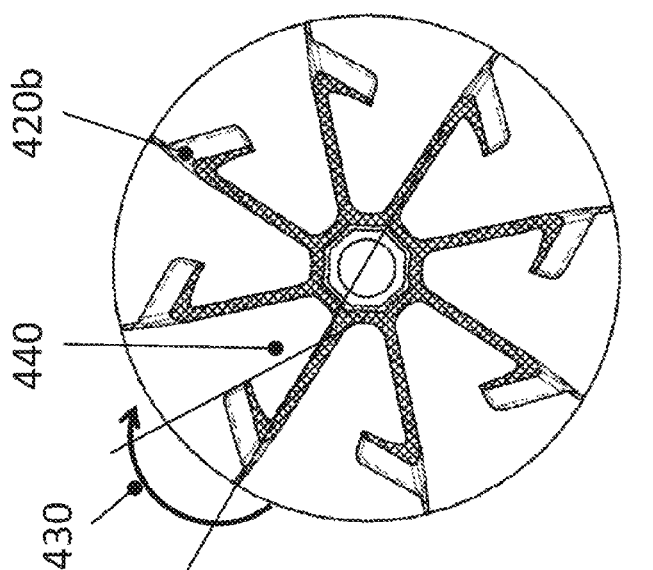
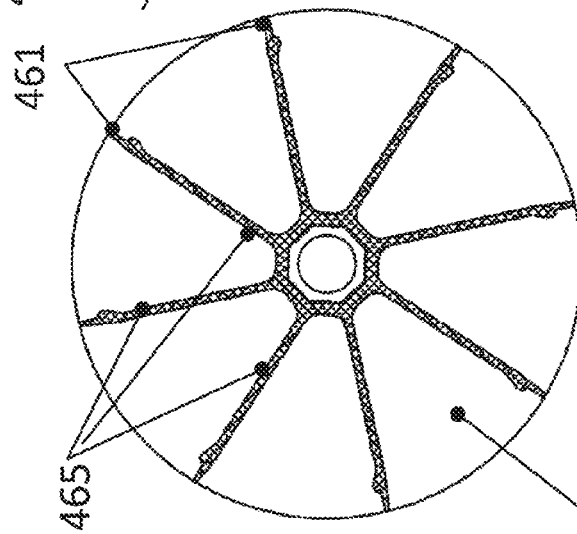
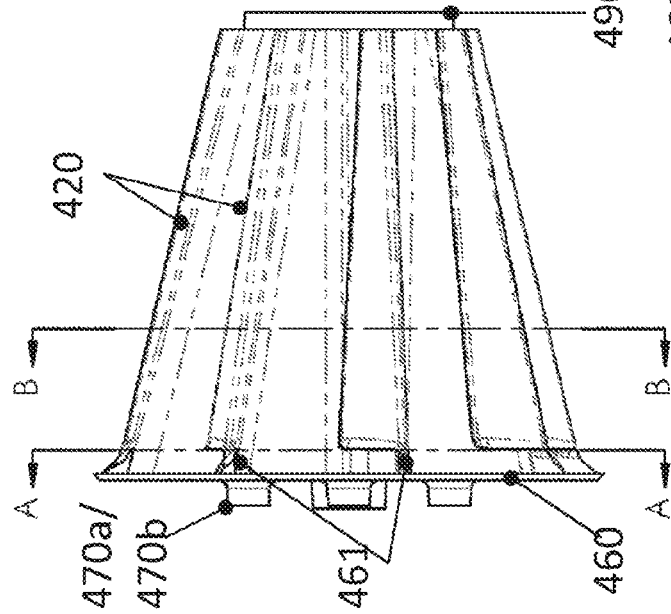
Section B-B
Figure 18c
Section A-A
Figure 18b
Figure 18a

| Electromagnetic signal analysis | 700 |

The electronic signal emitted by the angular velocity sensor 500 is saved as a digital file, either in its original form or as derivations thereof following electronic processing actions
710

A software algorithm extracts the chronological timestamps of the leading edge of the angular velocity sensor's 500 output
720

The timestamp of passage of each individual magnet 470a or LED 470b is extracted in relation to the initial timestamp datasets
730

The period of a full revolution is calculated per each individual permanent magnet 470a or LED 470b, thus removing errors from the timestamp data
740

Optionally use calibration curves to convert the timestamps of the individual magnets or LEDs to a calibrated flow rate for each individual magnet 470a or LED 470b.
750

The computed speed of rotation is optionally averaged among the plurality of magnets 470a or LEDs 470b, to determine the mean instantaneous flow rate
760

Optionally integrating the instantaneous flow rate over time to produce the total volume of urination
770

Optionally analyzing urine flow and urine volume data pertaining to individual urination sessions and to assess the probability of a medical condition, and assist a physician in the process of diagnosis.
780

Optionally analyze urine flow and urine volume data pertaining to individual patient over multiple urination sessions, to evaluate the progression of a specific patient's condition over time.
790

Figure 20

SYSTEM AND A METHOD FOR MEASUREMENT OF MOMENTARY URINE FLOW AND URINE VOLUME, AND THE ANALYSIS OF URINE FLOW PROPERTIES

FIELD OF THE INVENTION

The presented invention generally relates to the field of medical devices, and more specifically to methods of urine flow measurement and analysis.

DISCUSSION OF RELATED ART

U.S. Pat. No. 6,582,379B1 Stisen et al. teach an apparatus for measuring the discharge of a liquid, in particular urine, from a patient. The apparatus includes a measuring container (1), means (H) for applying a first acoustic signal to the liquid-empty part of the measuring container (1), means (H) for recording a second acoustic signal generated in the measuring container (1) in response to the first signal, means (45) for determining a current liquid amount in the measuring container (1) on the basis of the second acoustic signal. The measuring container (1) has a measuring pipe (5) defining a liquid-empty resonance chamber for generating the second acoustic signal.

JPH09220216A Fukahori et al. teach a urine flow rate measuring and analyzing device which is cost effective and inexpensive to allow easy installation as well as adopting the constitution to continuously measure the liquid level of the discharged urine flowing into a container for storing the discharged urine by ultrasonic waves, to determine its volume by the liquid level and to compute the flow rate of the discharged urine by a change in the volume with lapse of time. SOLUTION: An ultrasonic vibrator transducer 2 is mounted upward at the bottom end surface of the discharged urine measuring container 1a constituting the container 1 for storing the discharged urine. A dummy acoustic bonding layer 3 is formed in the upper layer to the ultrasonic vibrator transducer 2, and further, an acoustic bonding material 4 is formed atop the layer. The acoustic bonding material 4 forms the container inside base of the discharged urine measuring container 1a constituting the container 1 for storing the discharged urine. The ultrasonic vibrator transducer 2 emits the ultrasonic waves toward the inside of the discharged urine measuring container 1a constituting the container 1 for storing the discharged urine through the dummy acoustic bonding layer 3 and the acoustic bonding material 4, thereby playing a function to receive the reflected waves reflected at the boundary between the urine and the air layer through the acoustic bonding material 4 and the dummy acoustic bonding layer 3.

JPH09248289A Fukahori et al. teach a urine vessel 1 for urine flow measurement and analysis equipment is to measure urine flow of mankind using the ultrasonic wave so that measured data are used for urologic therapy and diagnosis. For this purpose, the urine vessel 1 is detachably hung in a way that the tapered side of the vessel directs downward. Inside the urine vessel 1, upward, from the center of the tapered bottom a urine measurement cylinder 2 is installed, with small holes at its bottom so that the urine enters the cylinder 2 through the holes. Under the bottom of the urine measurement cylinder 2, an ultrasonic vibrator 5 is attached to radiate the ultrasonic wave to the urine level in the urine measurement cylinder 2 and to receive the reflected wave.

US20050256428 A1 Aundal et al. teach an open circuit gravity-assisted uroflowmeter has a urine collector having a generally open inlet in fluid communication with a sensing passage located at a lower elevation than the inlet, the sensing passage intersecting a magnetic field and having electrodes for detecting a flow-dependent voltage induced by the passage of urine through the magnetic field. Preferred embodiments of the uroflowmeter may have low pressure drop, rapid response and simple construction.

DE 3007855 A1 Fuchs et al. teach a device which has a funnel receiving the urine coupled to a housing containing flowmeter suspended to be free to oscillate. It comprises a U-shaped measuring tube inclined at a slight angle to the horizontal coupled to the outlet of the funnel at one end, and with an outlet projecting outside the housing. A measuring element responds to the oscillation of the tube during urination to supply a signal to an evaluation unit. Pref. the tube acts on a spring blade fixed to the housing at one end and facing a fixed differential field measuring element at the other end.

U.S. Pat. No. 6,079,280 A Miller et al. teach a flow sensor using induction pickup and having an improved paddle wheel type impeller within an impeller housing having a concave opening defining a protective skirt area for shielding a portion of the paddle wheel and a stem of the paddle wheel with a varying thickness for reducing cavitational backflow and therefore achieving a precise measurement of the fluid flow velocity and a high turndown ratio is disclosed.

WO 2009/143113 A1, The University Of Vermont And State Agricultural College teach systems for and methods of assessing lower urinary tract function from urinary flow data via sound analysis and user-provided information regarding the lower urinary tract symptoms (LUTS) of frequency, urgency and urge incontinence. Embodiments of the LUTS assessment systems include a computer and a telephone or a digital recording mechanism to capture the sound of one or more urination events, which are stored as audio files in a database. The LUTS assessment systems may include sound analysis software for analyzing the strength and duration of each urination event and may include a web-based software application for viewing the results via the Internet or other network. The database stores information from multiple urination events, and combined with information regarding the lower urinary tract symptoms, serves as an objective tool to assess bladder function and monitor progression of disease or therapy effectiveness.

SUMMARY OF THE INVENTION

The present invention provides an apparatus for physically measuring and monitoring the exact volume and momentary flow rate of urine produced by an individual during a urination session.

According to some embodiments, the apparatus comprises:
  an encasement 200, configured to encase components of said apparatus;
  a receptacle bowl 100 attached to said encasement, configured to be placed over a toilet bowl or seat, and direct fluid through a single point of exit 110 to a fluid flow guide 600;
  the fluid flow guide, configured to transfer fluid from the receptacle bowl 100 to an impeller 400;
  the impeller 400, configured to rotate along a rotation axis 400a, wherein said impeller 400, comprises a plurality of blades 420, configured to receive the urine from the flow guide, and thereby rotate the impeller 400 at a speed correlating with the flow rate of the urine; and an angular velocity sensor 500, configured to produce electric signals that correlate with the angular velocity or angular position of the impeller 400.

According to some embodiments, the apparatus further comprises a shaft 410 that is fixed onto the encasement 200, wherein the impeller 400 is mounted onto said fixed shaft via at least one low friction hub 411a and/or bearing 411, and is free to rotate in respect to the shaft along the rotation axis 400a.

According to some embodiments, the impeller 400 is fixedly mounted on a shaft 410, and the shaft 410 is connected to the encasement 200 via at least one low friction hub 411a and/or bearing 411, enabling the impeller to rotate along the rotation axis 400a.

According to some embodiments, the impeller is installed within the apparatus' encasement 200 via at least one low friction hub 411a and/or bearing 411, and is free to rotate by said low friction hub and/or bearing along the rotation axis 400a.

According to some embodiments, the impeller 400 further comprises a plurality of permanent magnets 470a, located radially on the impeller's distal end, and wherein the angular velocity sensor 500 comprises a stationary Hall effect sensor 500a, configured to sense an electromagnetic signal induced by the proximate passage of said permanent magnets 470a, during rotation of the impeller, to produce the electric signals.

According to some embodiments, the impeller further comprises a plurality of LED light sources 470b, located radially on the impeller's distal end, and wherein the angular velocity sensor 500 comprises a stationary photodiode sensor 500b, configured to sense the light emitted from said LEDs during proximate passage of said LEDs during rotation of the impeller, to produce the electrical signals.

According to some embodiments, the angular velocity sensor 500 comprises a rotary encoder 500c mounted to the shaft 410, and configured to sense rotation of the shaft and responsively to the sensed rotation to produce the electrical signals.

According to some embodiments, the apparatus further comprises an electronic circuit 510 configured to receive the electric signals from the angular velocity sensor 500 and responsively to determine a momentary rate of urine flow.

According to some embodiments, the apparatus further comprises electronic circuit 510 configured to receive the electric signals from the angular velocity sensor, and to transmit the electric signals or derivations thereof by wireless or wired communication to a remote processor, configured to determine a momentary rate of urine flow during urination.

According to some embodiments, the receptacle bowl 100 comprises radial ribs 130, configured to reduce the flow momentum of the urine, prevent fluid from flowing around the receptacle bowl 100, and direct the fluid towards the bowl's single point of exit 110 with minimal delay.

According to some embodiments, the receptacle bowl 100 further comprises concentric steps 140, configured to prevent fluid from flowing upwards, along the sides of the bowl, and direct fluid towards the bowl's single point of exit 110 with minimal delay.

According to some embodiments, the flow guide 600 comprises an inlet 110, configured to enable ingress of fluid from the receptacle bowl 100, and an outlet 310, configured to enable egress of fluid onto the impeller 400, and wherein the flow guide is inclined in two planes, to provide free draining of fluid from said inlet 110 to said outlet 310 and onto said impeller 400, and wherein said inclination of the flow guide is configured to cause fluid droplets to overcome the retaining force of fluid surface tension and be directed towards the impeller 400 with minimal delay.

According to some embodiments, the outlet 310 is located in close proximity to the impeller, and transfer of individual droplets from the flow guide 600 to the impeller is promoted by the formation of a drop at the said single outlet location 310 of the flow guide, such that:

the gap 315 between the flow guide and the impeller is configured so that the fluid droplet, during its formation, contacts the impeller and flows onto the impeller, and is hence captured by the impeller at the earliest opportunity; and said gap is configured so as to ensure that the surface tension of the fluid cannot cause fluid droplets to affix to both the impeller and flow guide at the same time due to surface tension.

According to some embodiments, the flow guide 600 comprises a reservoir 610, configured to capture a known volume of incoming fluid from the receptacle bowl 100, during an initial phase of urination, and fill up to a known height, before allowing the fluid to proceed towards the impeller 400.

According to some embodiments, the reservoir 610 comprises a plurality of vertically oriented baffles 620, arranged in an array within the reservoir, so as to absorb the kinetic energy of the fluid flowing through the reservoir.

According to some embodiments, the distance between adjacent baffles within said array is configured so as to utilize the fluid tension produced by the fluid's contact with said baffles to extract air bubbles from the fluid and prevent turbulence in the fluid, and wherein said distance is configured so as to accommodate the expected range of fluid flow rates, and avoid a backup flow of fluid.

According to some embodiments, the reservoir 610 is bordered by a vertical cascade wall 630 on one side, configured to enable fluid to flow over said cascade wall when the level of fluid in the reservoir surpasses the height of the cascade wall, and wherein the cascade wall is installed above the impeller 400, so as to direct said flow of fluid onto the impeller blades 420 to produce torque and rotate the impeller 400.

According to some embodiments, the top surface of said cascade wall has a smooth, round cross section, producing a laminar flow of fluid over the said cascade wall, and wherein the bottom side of said cascade wall comprises a sharp lower edge, configured to release the fluid in a laminar flow onto said impeller blades.

According to some embodiments, the apparatus further comprises a physical restrictor wall 650, installed in a vertical plane parallel to that of the cascade wall 630, forming a vertical gap 670 between the two said walls, wherein said vertical gap facilitates the flow of fluid therein, from the reservoir 610 onto the impeller blades 420, and wherein the bottom side of said physical restrictor wall comprises a sharp lower edge, configured to release the fluid in a laminar flow onto said impeller blades.

According to some embodiments, the height of the cascade wall 630 is angled in respect to the horizontal plane, so as to initiate laminar flow of fluid over the cascade wall 630 at the proximal side 630d onto the proximal side of the impeller blades 420, and consistently dispense laminar flow of fluid over an increasingly longer portion of the cascade wall 630, and onto an increasingly longer portion of the impeller blades 420 as the flow of fluid is increased.

According to some embodiments, the cascade wall 630 comprises a groove at the location of the cascade wall's top, proximal side 630*d*, said groove configured to initiate the flow of fluid over the cascade wall 630 at the wall's proximal side 630*d*.

According to some embodiments, the cascade wall 630 further comprises a sharp lip at the location of the wall's top, distal side 630*e*, configured to prevent the fluid from over flowing on the cascade wall's the distal side 630*e*, and bias the flow of urine towards the cascade wall's proximal side 630*d*.

According to some embodiments, the reservoir further comprises a drain aperture 640, located at the bottom of said cascade wall 630, and is configured to enable evacuation of fluid from said reservoir onto the impeller blades 420 in a constant, known rate and in a constant, known position, configured in respect to the expected range of urine flow rates, so as to enable filling the reservoir with fluid during the initial phase of urination, and wherein said drain aperture is configured to enable complete evacuation of fluid from the reservoir after the end of urination.

According to some embodiments, the blades 420 are curved so as to creating a concavity having a defined volume, enabling the impeller blades to capture fluid therein, and retaining it on the impeller, until the mass of the collected fluid exceeds the rotating friction of the impeller, and the impeller is made to rotate.

According to some embodiments, the distance of said concavities in relation to the axis of the impeller's rotation is configured so that said known amount of fluid creates torque that overcomes retaining friction forces applied to the impeller, and rotate the impeller.

According to some embodiments, the rotation axis 400*a* is inclined with respect to the horizontal plane such that fluid captured by the blades is directed to flow axially along the impeller blade, from the impeller's proximal side towards the impeller's distal end, and wherein said inclination is configured to enable fluid droplets overcome the retaining force of fluid surface tension and be directed towards the impeller's distal end.

According to some embodiments, the impeller 400 further comprises a flange 460, attached to said blades in a perpendicular plane to the impeller's rotation axis, at the distal end of said impeller 400, and wherein an aperture in the said attachment enables fluid to evacuate the blades onto the surface of said flange.

According to some embodiments, the flange 460 has a larger diameter than that of the blades 420, to increase fluid evacuation of the impeller due to the centrifugal force of the rotating impeller 400.

According to some embodiments, the rim of the said flange has a thin cross-section, to minimize the adherence of droplets to the lowermost edge of the impeller due to surface tension.

According to some embodiments, the flange 460 comprises vanes 465, dividing the face of the flange to sections, said vanes configured to restrict the fluid from passing from one section to another, and direct the fluid in a radial direction, thus evacuating the fluid from the face of the flange towards the toilet's drain with minimal delay.

According to some embodiments, the apparatus further comprises a friction cap 495, attached to the impeller, in a plane that is perpendicular to the impeller's rotation axis.

According to some embodiments, the apparatus further comprises a spring coil 497 and a beam 496, wherein:
  said spring coil is attached to the apparatus' encasement on one end and attached to said beam on the other end;
  said spring coil is configured to exert a constant force on said beam; and
  said beam is configured to constantly brush against said friction cap during rotation of the impeller to produce a friction force on the friction cap as a result of said constant force exerted by the coil.

According to some embodiments, the apparatus further comprises at least one clutch plate 498, installed within the encasement, and is configured to apply a friction force upon the friction cap 495 to produce said stopping force.

DESCRIPTION OF THE DRAWINGS

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

It is to be understood that the terms "including", "comprising", "consisting" and grammatical variants thereof do not preclude the addition of one or more components, features, steps, or integers or groups thereof and that the terms are to be construed as specifying components, features, steps or integers.

Figure 1:
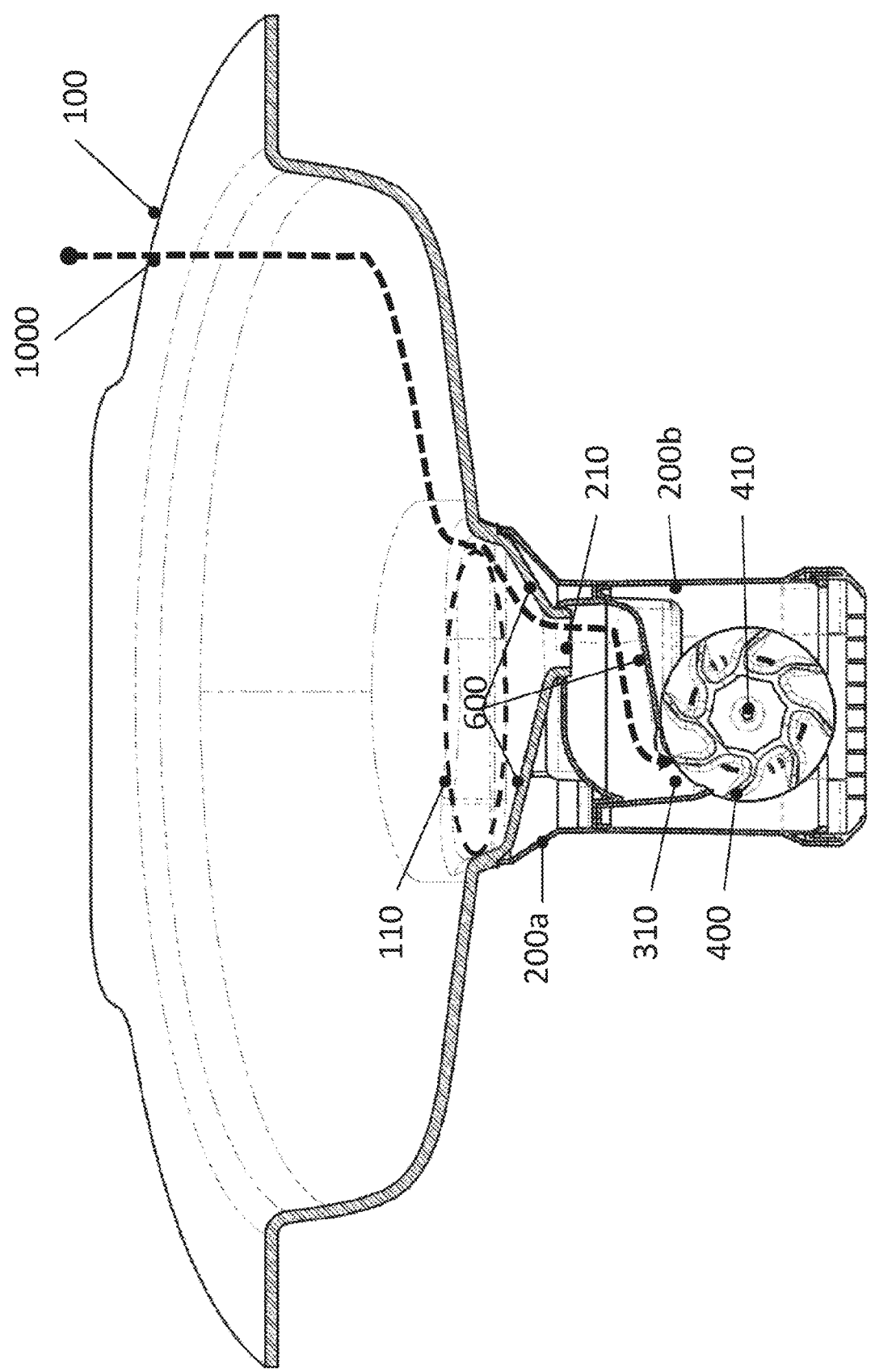

If the specification or claims refer to "an additional" element, that does not preclude there being more than one of the additional element.

It is to be understood that where the claims or specification refer to "a" or "an" element, such reference is not to be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

The term "fluid" may refer to urine, water or any other liquid that is made to flow through the apparatus of the present invention, for the purpose of measuring the fluid's flow rate.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of some embodiments of the invention shall not be construed as an admission that such reference is available as prior art to the present invention.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

FIG. 1 presents a section view of the flow meter apparatus, including a bowl, an encasement, a fluid guide and an impeller, and presents the flow of urine according to some embodiments of the present invention.

Figure 2:
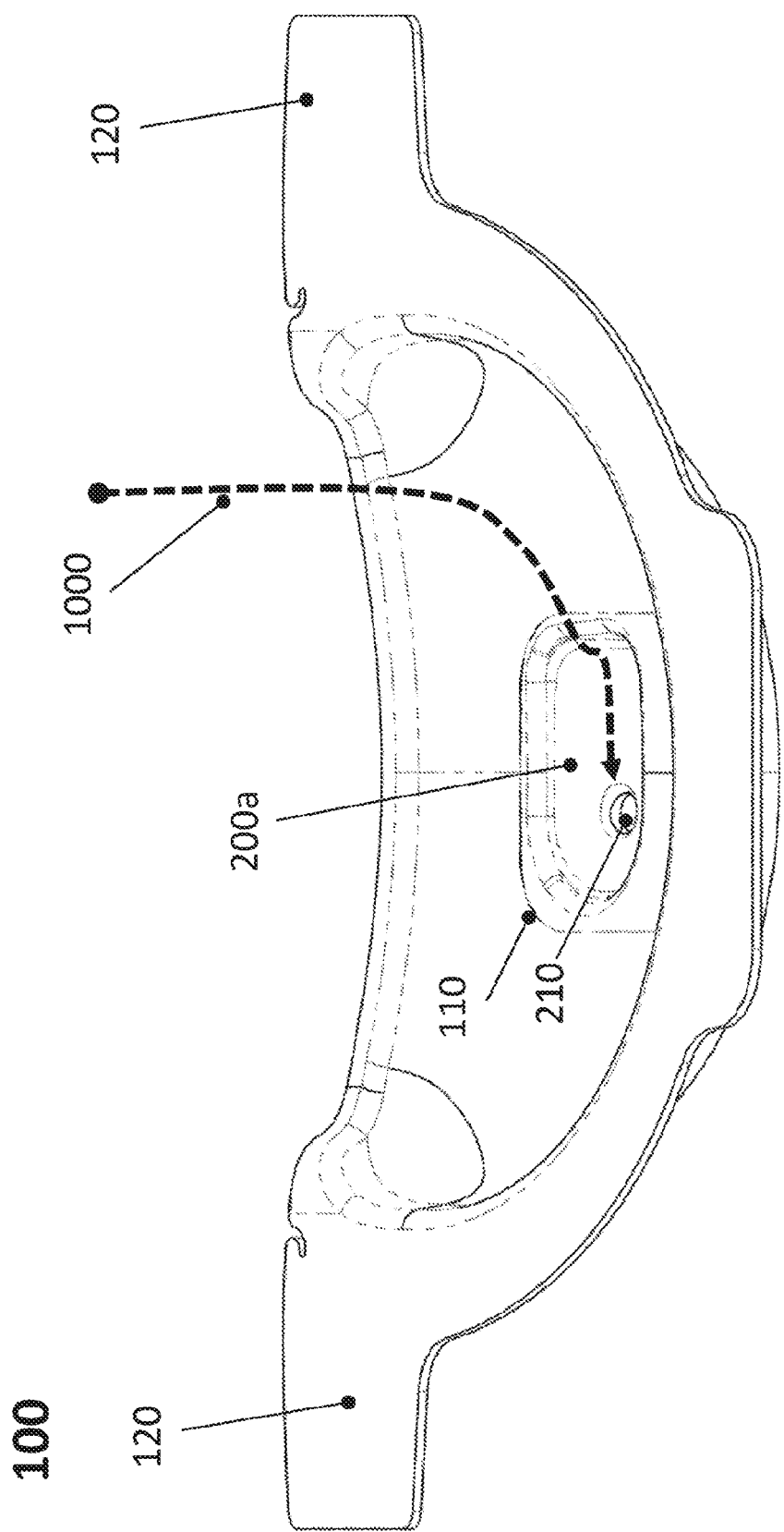

FIG. 2 presents an elevated perspective view of the receptacle bowl 100, including at least one flap 120 for the purpose of hanging the apparatus over a toilet seat or toilet bowl, according to some embodiments of the present invention.

Figure 3:
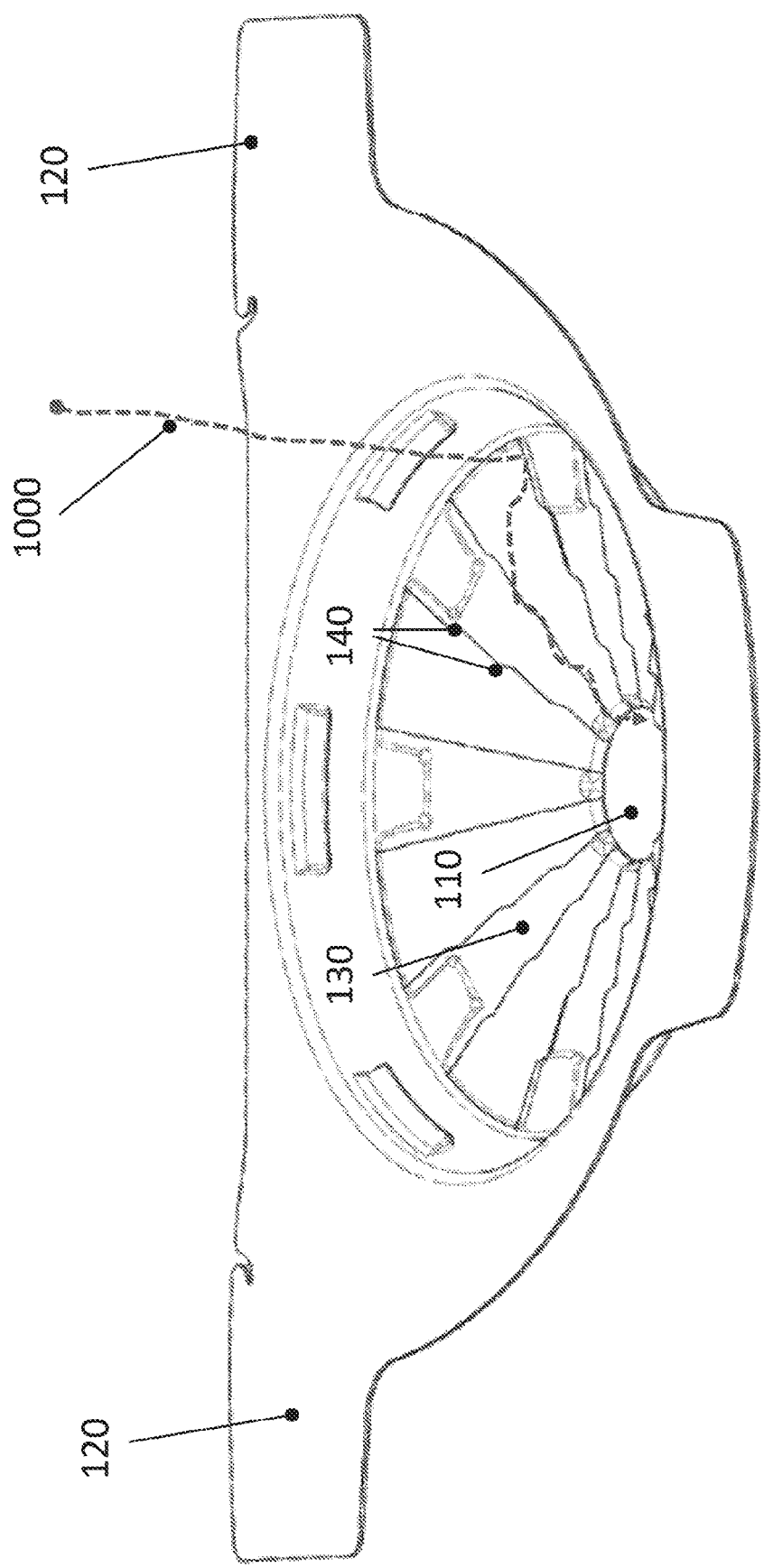
Figure 4:
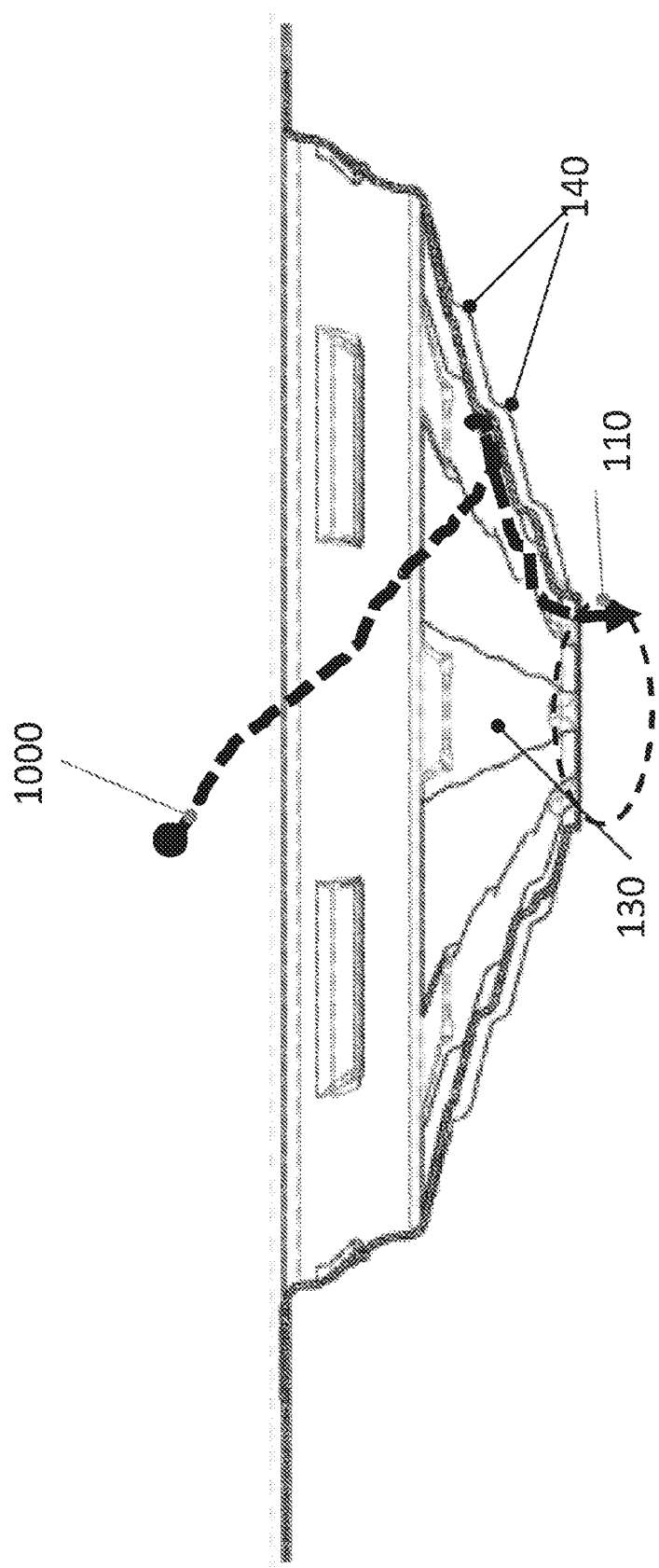

FIGS. 3 and 4 respectively present an elevated view and a frontal view of the receptacle bowl 100, according to additional embodiments of the present invention.

Figure 5:
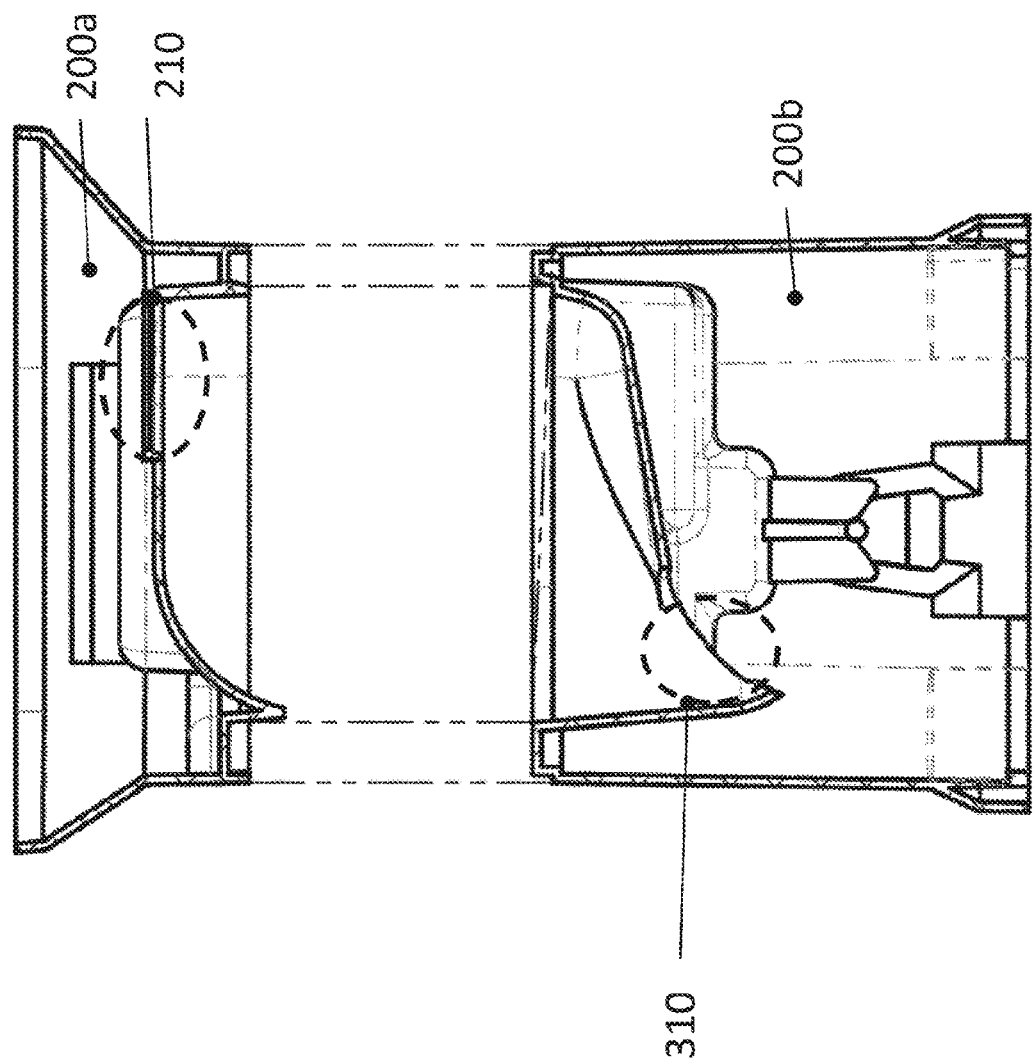

FIG. 5 presents an exploded perspective view of the apparatus' encasement, distinguishing between an upper encasement part and a lower encasement part, according to some embodiments of the present invention.

Figure 6:
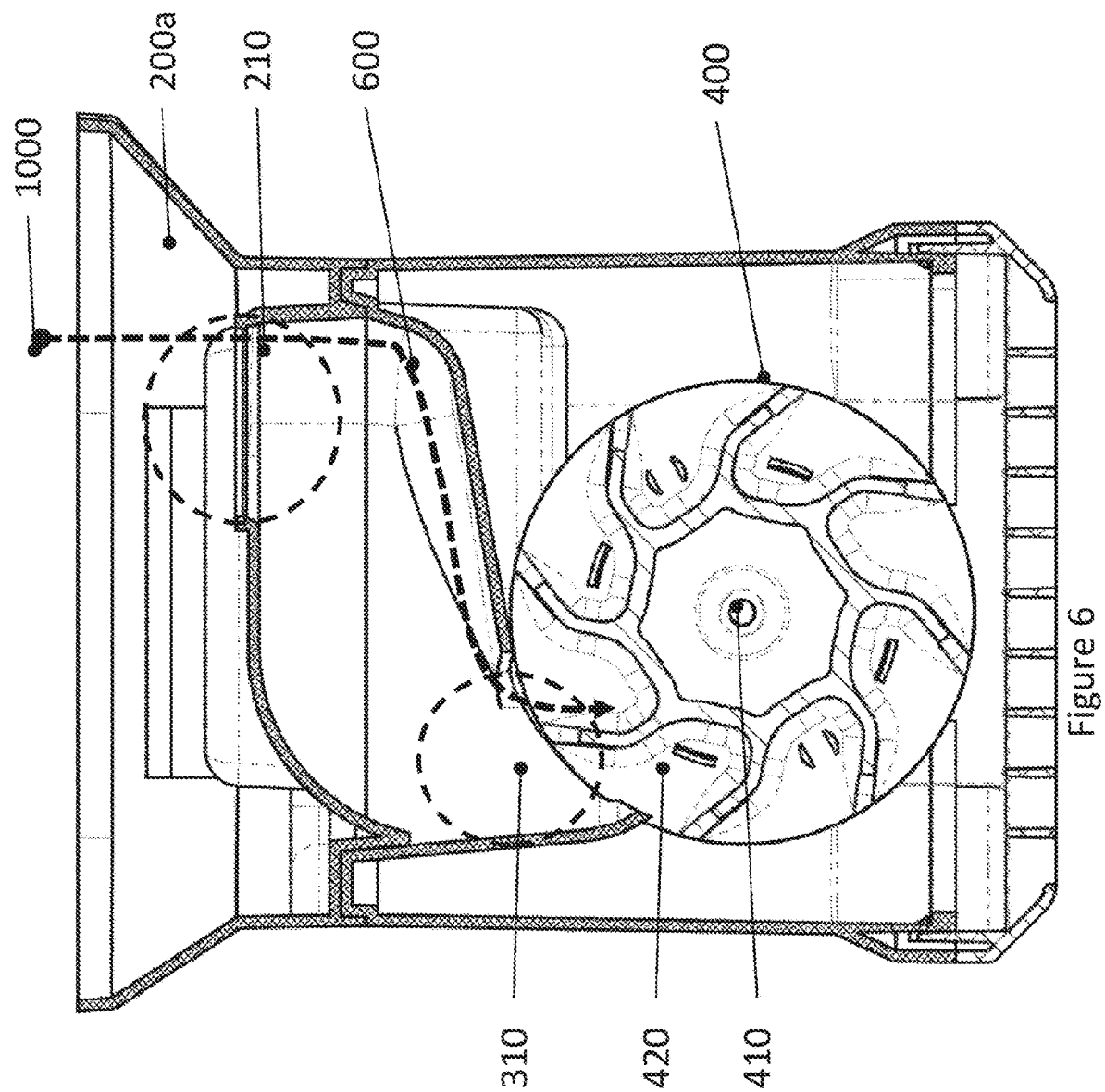

FIG. 6 presents a front section view of the upper and lower encasement parts, including the flow guide and impeller, according to some embodiments of the present invention.

Figure 7:
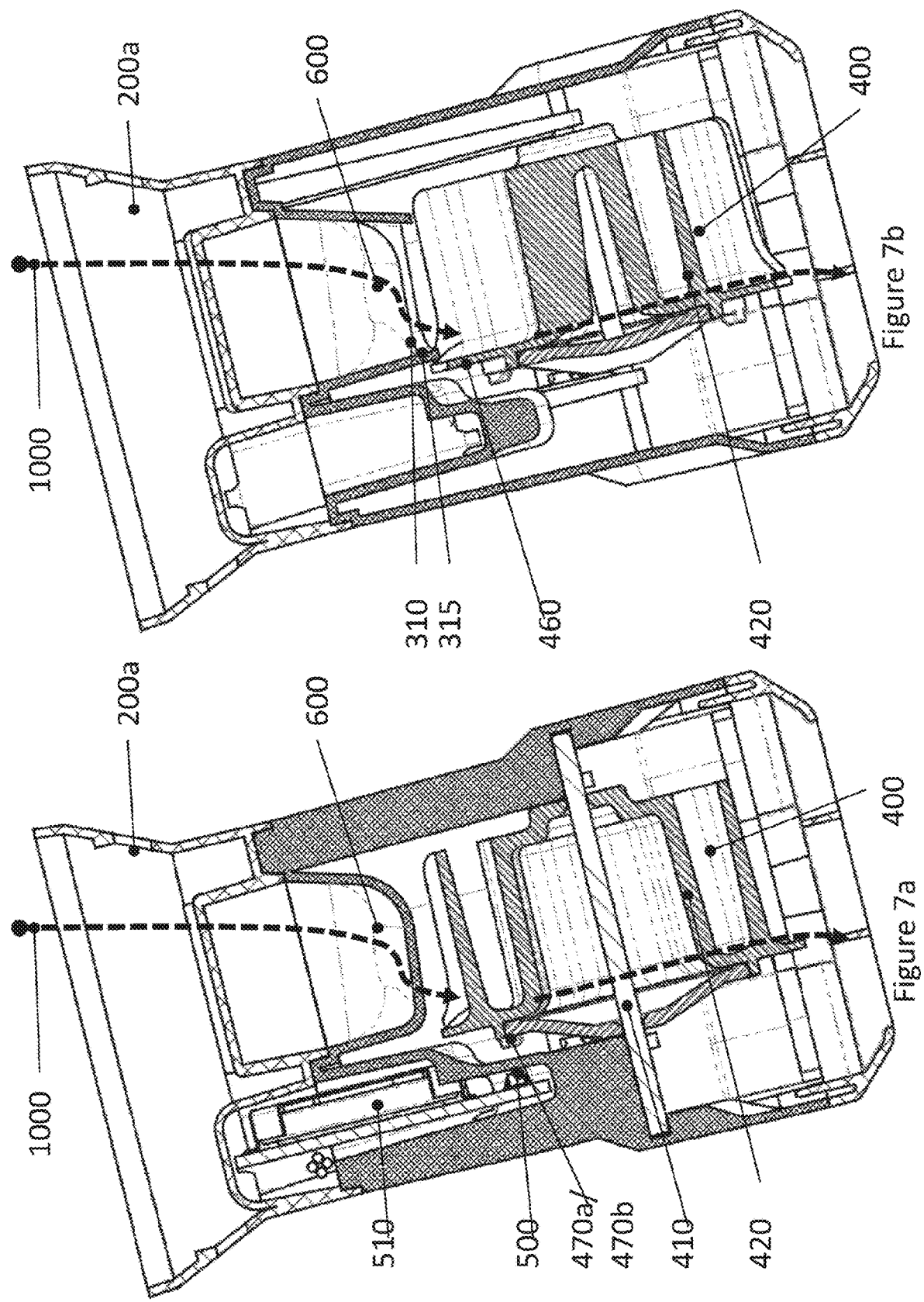

FIGS. 7a and 7b respectively show distal and proximal lateral section views of the flow meter assembly of an embodiment of the present invention, illustrating the fluid path from the fluid flow guide onto the impeller and therefrom, according to some embodiments of the present invention.

Figure 8:
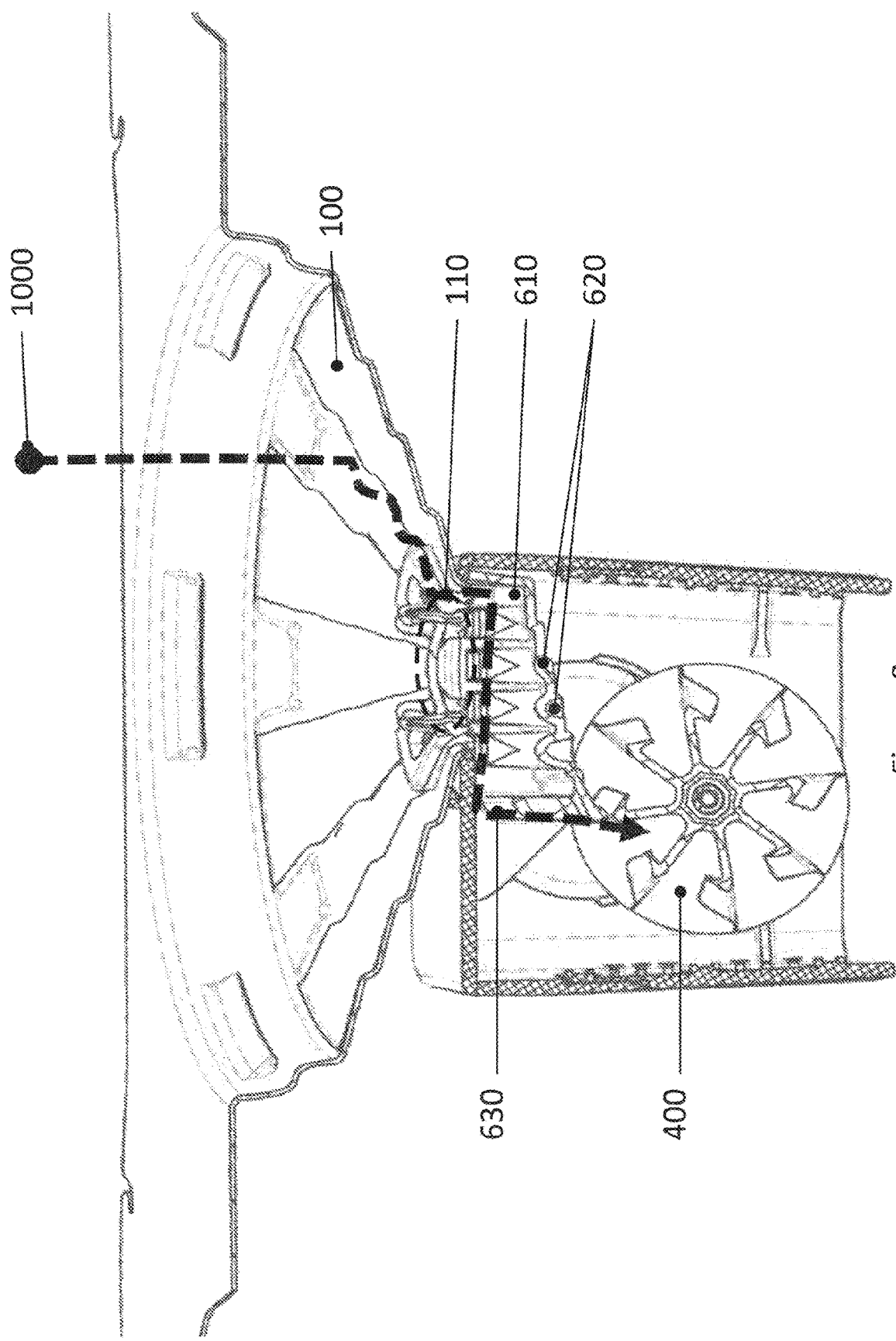

FIG. 8 presents a section view of the flow meter apparatus, including a bowl, an encasement, a fluid guide comprising a reservoir and an impeller, and presents the flow of urine according to some embodiments of the present invention.

Figure 9:
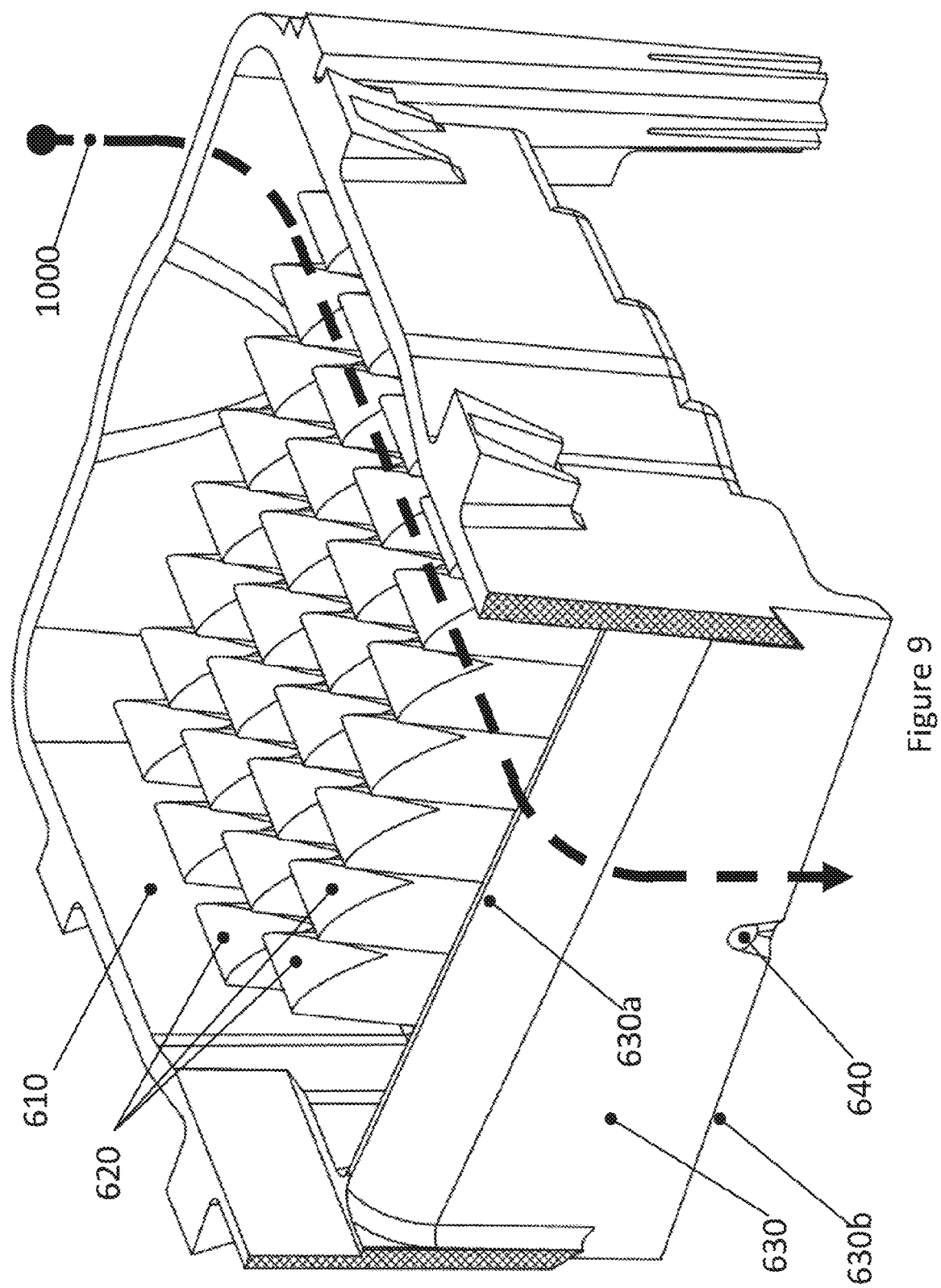

FIG. 9 presents an elevated isometric view of the reservoir according to some embodiments of the present invention.

Figure 10:
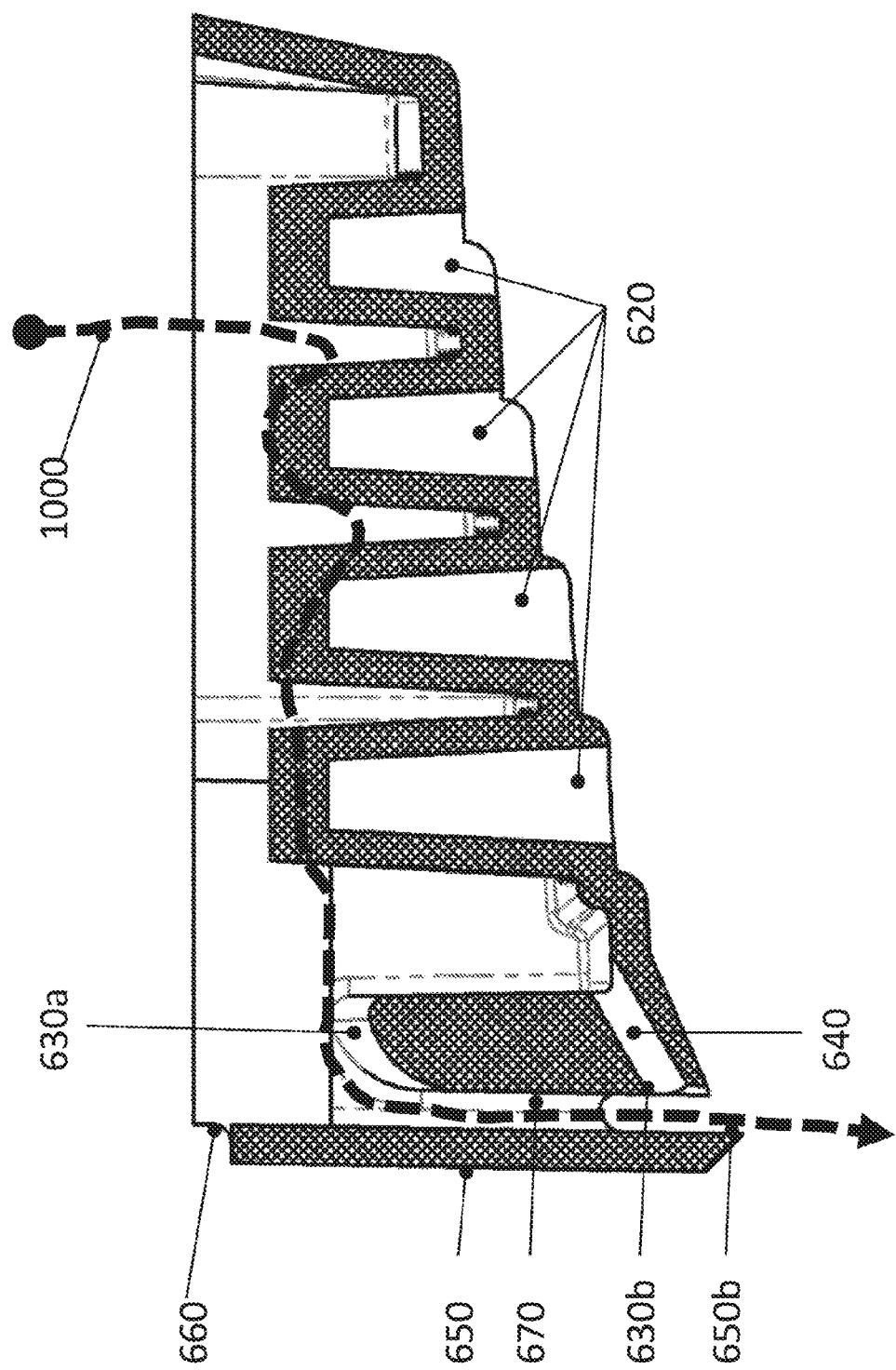

FIG. 10 presents a front section view of the reservoir and cascade wall according to some embodiments of the present invention.

Figure 11:
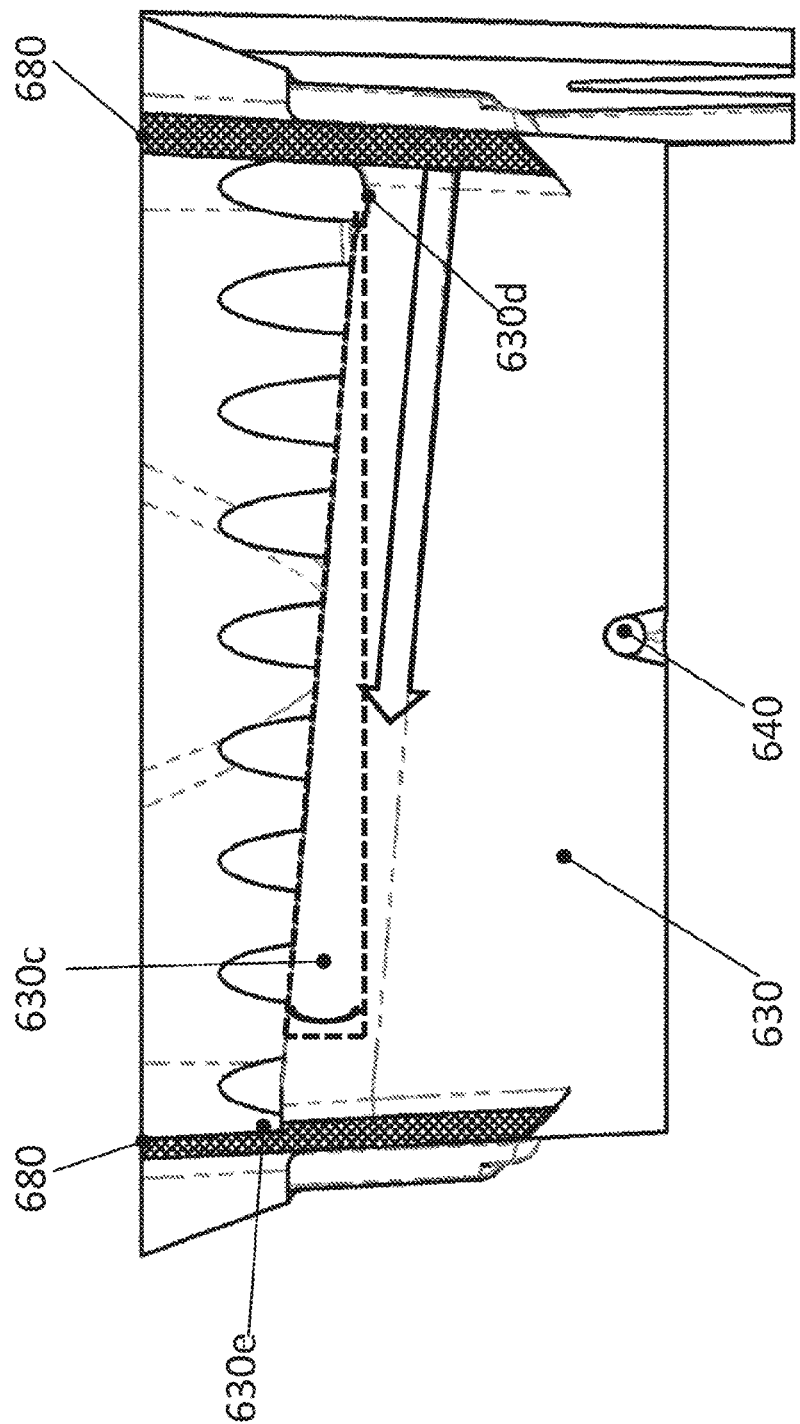

FIG. 11 both presents a lateral view of the reservoir and cascade wall according to some embodiments of the present invention.

Figure 12:
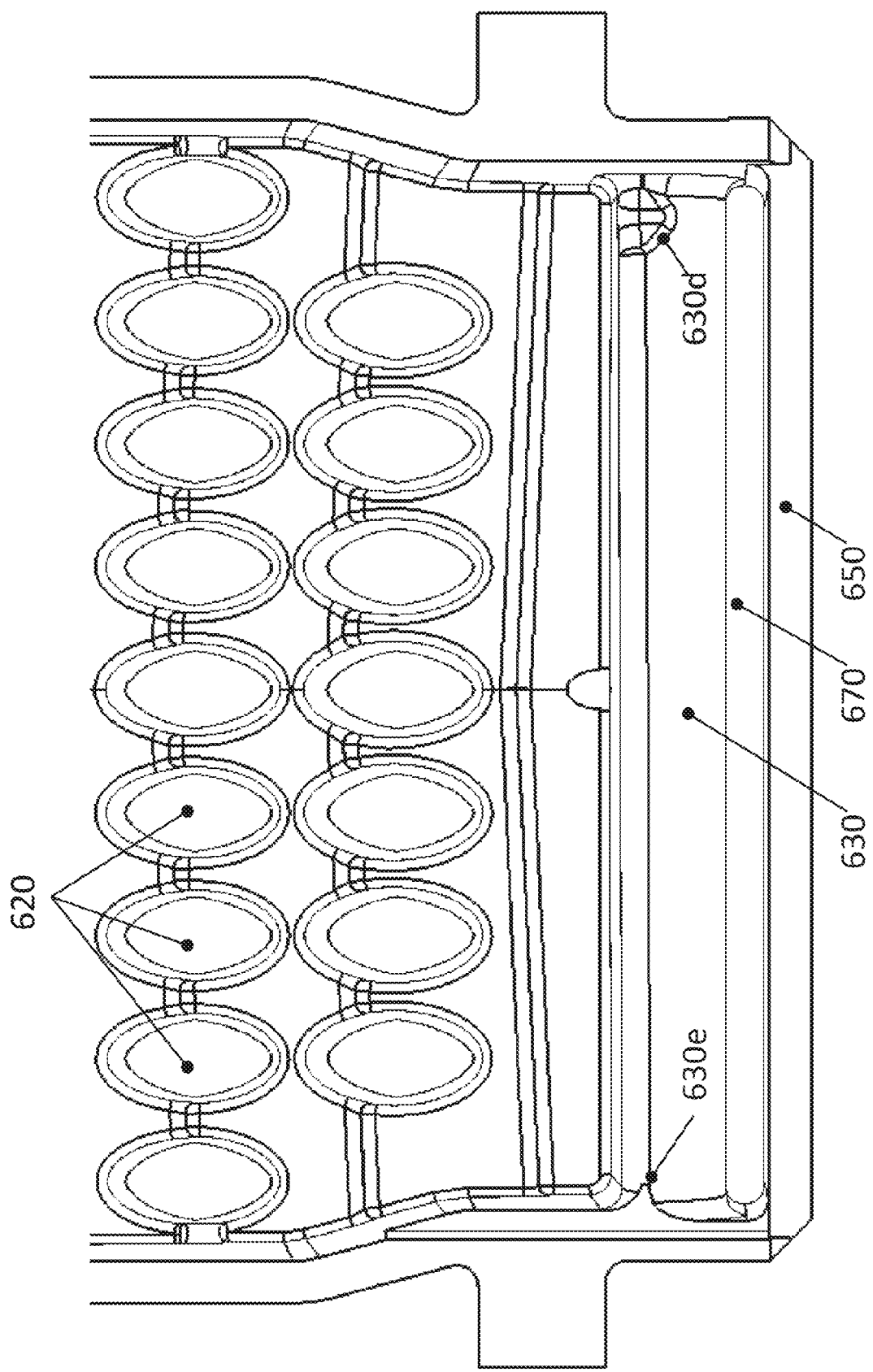

FIG. 12 depicts a top view of the cascade wall and its surroundings according to some embodiments of the present invention.

Figure 13:
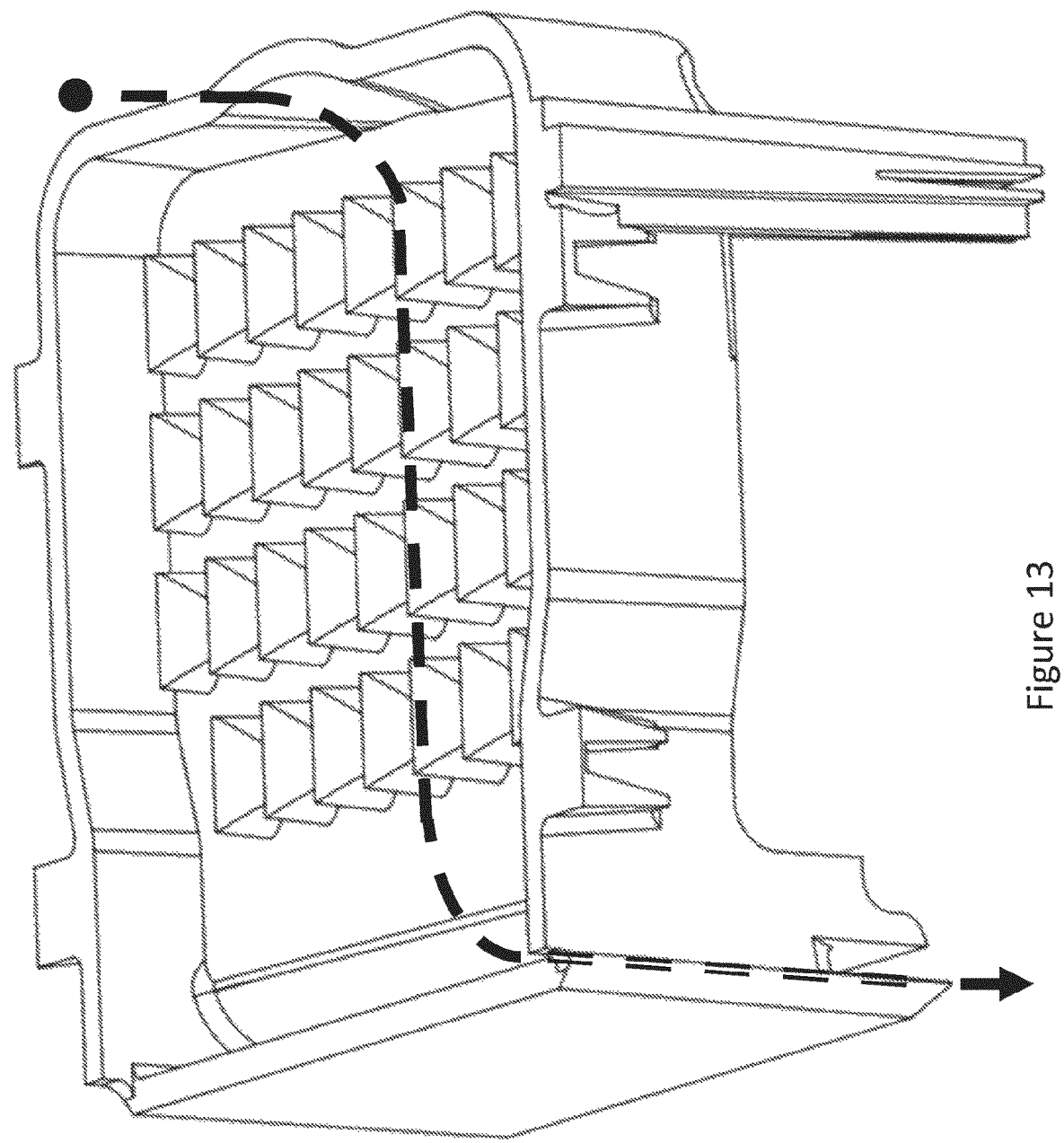

FIG. 13 presents an elevated isometric view of the reservoir and cascade wall according to some embodiments of the present invention.

Figure 14B:
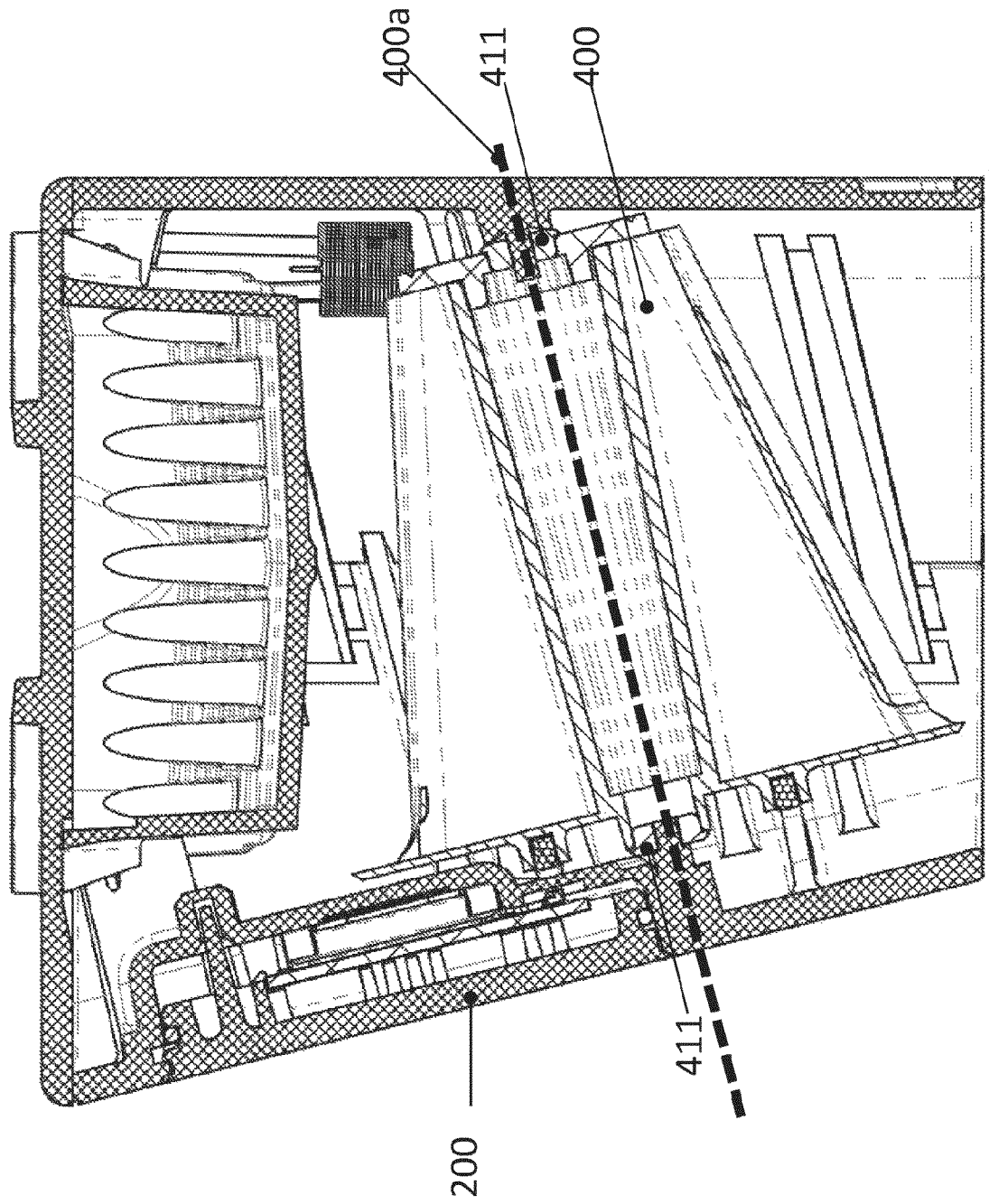

FIGS. 14a and 14b are lateral section views of the encasement and the elements residing within the encasement, and the path of urine flow, according to some embodiments of the present invention.

Figure 15:
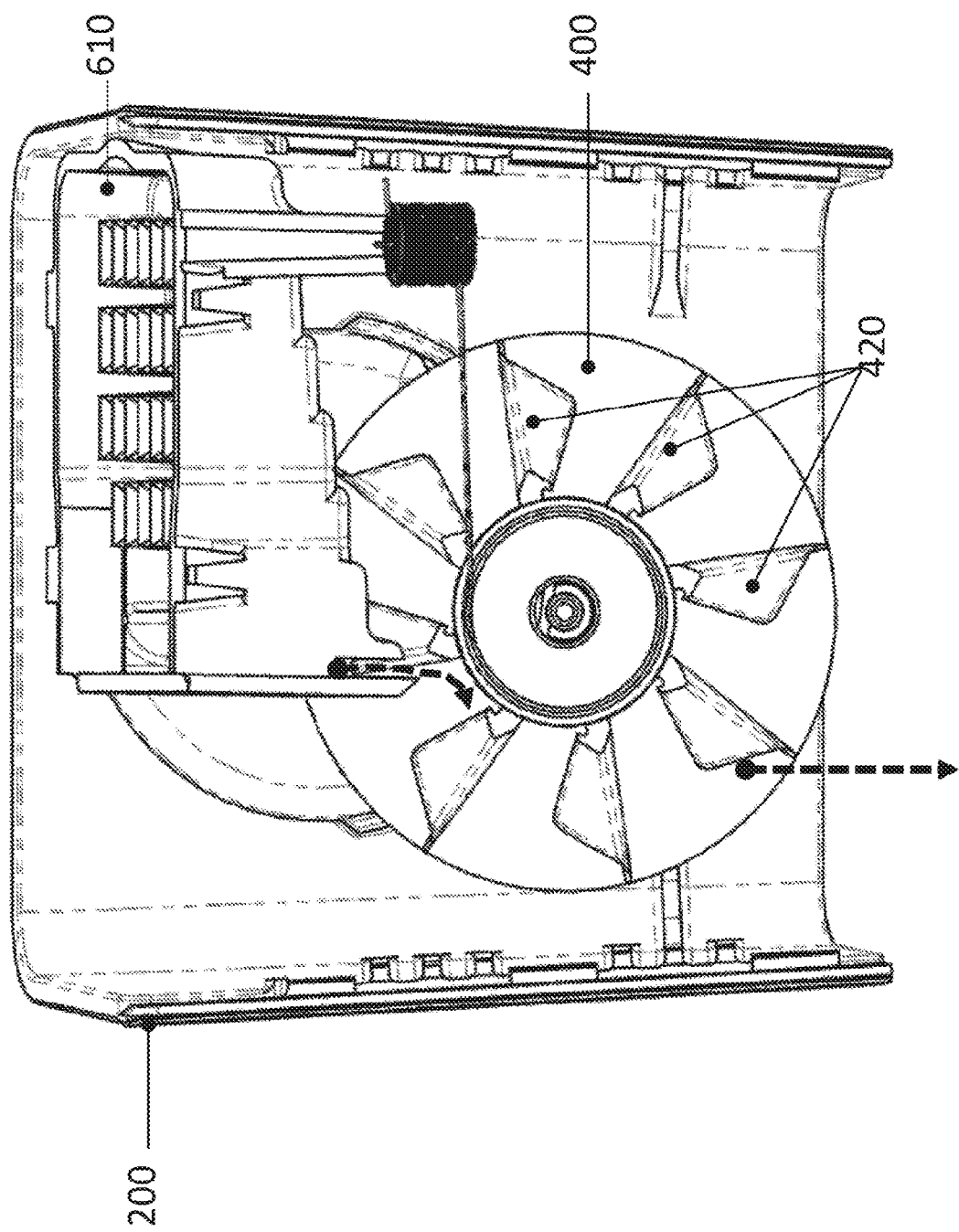

FIG. 15 is a front section view of the apparatus, presenting the path of urine flow onto the impeller, and therefrom to the toilet drain, according to some embodiments of the present invention.

FIGS. 16a and 16b respectively show a front view and a lateral section view of the impeller, presenting the location of permanent magnets, and the concavities formed by the impeller's blades, according to some embodiments of the present invention.

FIGS. 17a and 17b respectively present a front view and a section view of the impeller, according to some embodiments of the present invention.

FIGS. 18a, 18b and 18c respectively present a lateral view, and two section views of the impeller, according to some embodiments of the present invention.

Figure 19A:
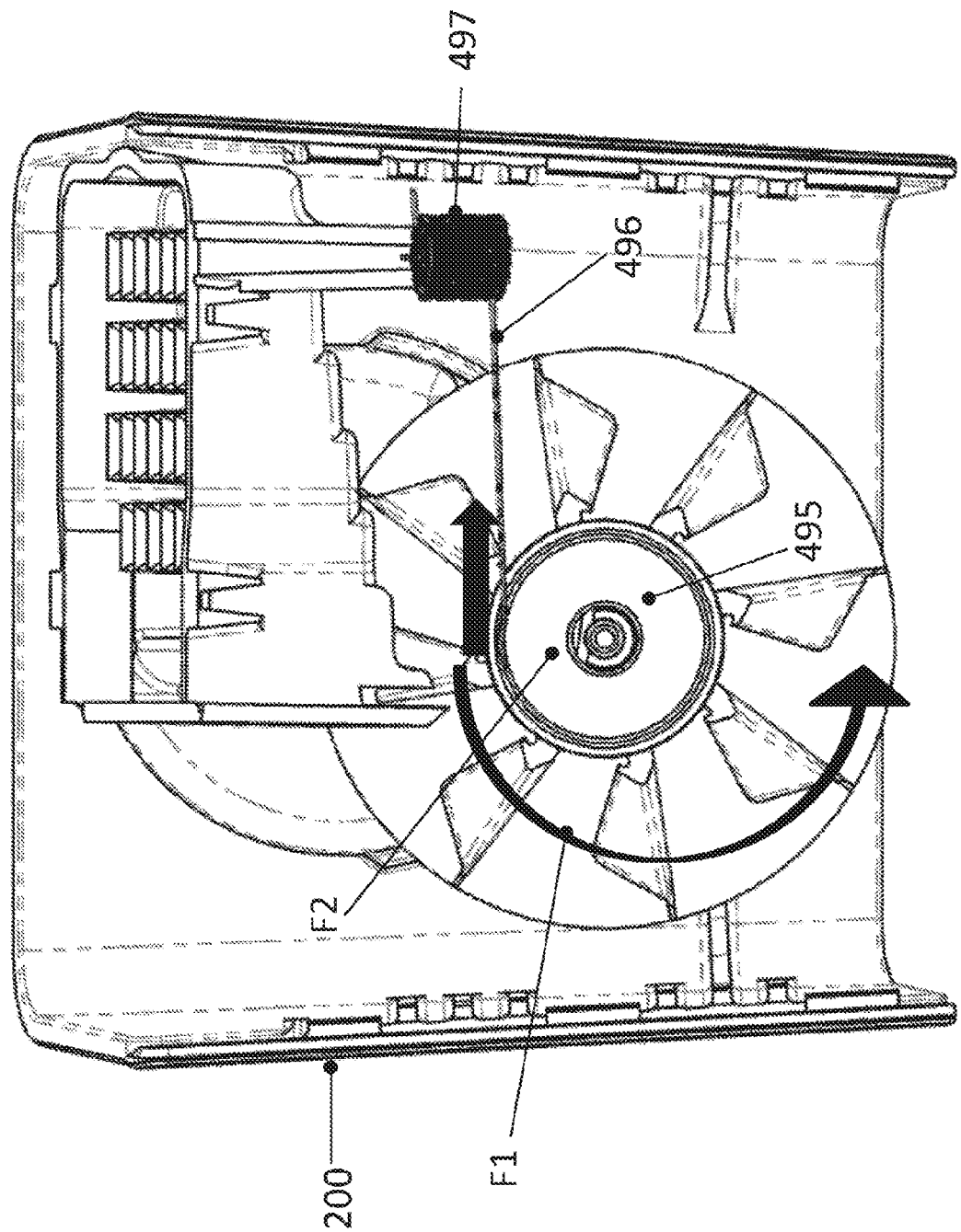
Figure 19B:
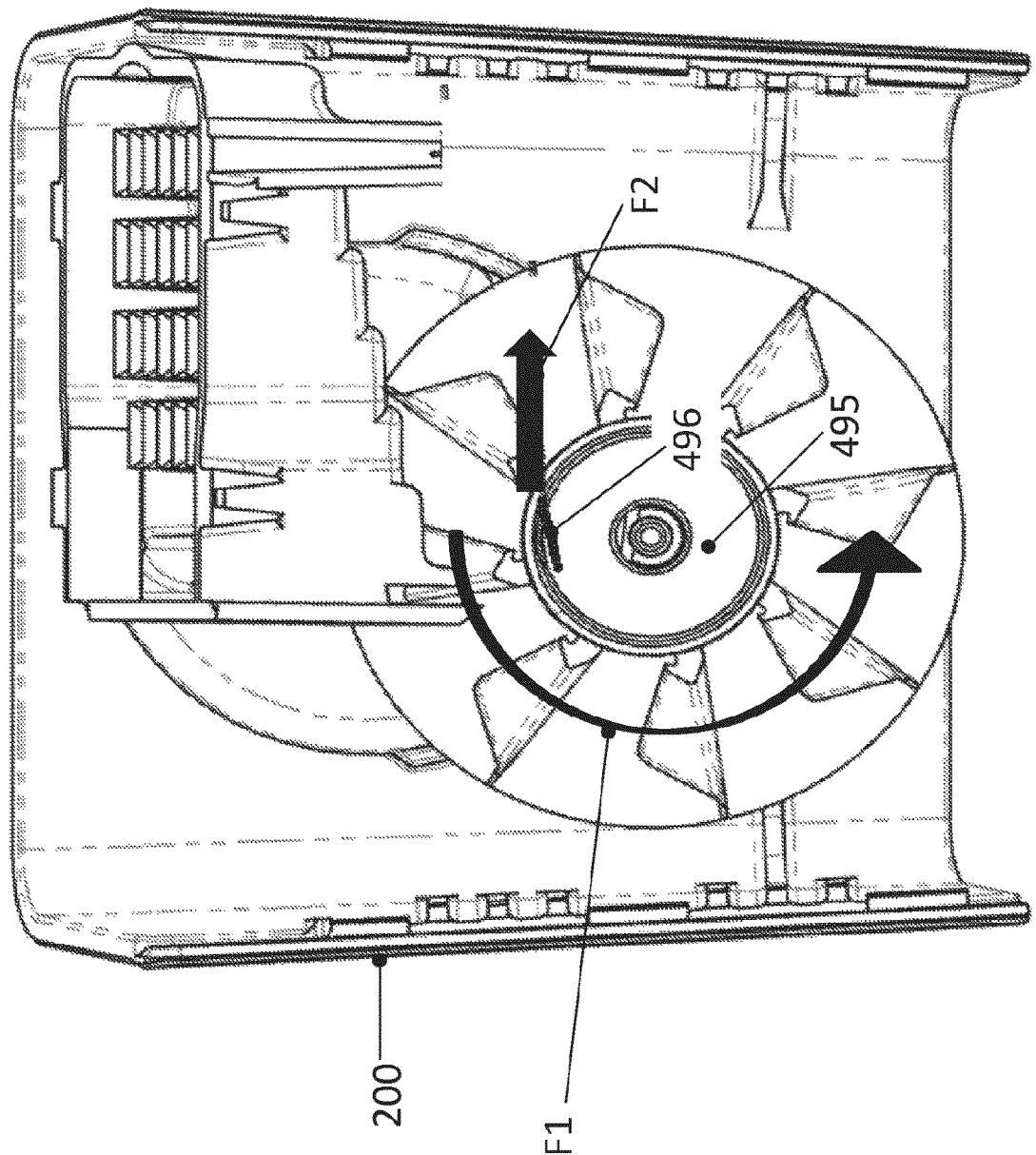

FIGS. 19a and 19b are front section views of the encasement, presenting the torque exerted by different forces applied on the impeller, according to some embodiments of the present invention.

FIG. 20 is a flow diagram elaborating the analysis of data extracted from the angular velocity sensor, according to some embodiments of the present invention.

DETAILED DESCRIPTION OF SOME EMBODIMENTS OF THE INVENTION

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The present invention provides an apparatus for physically measuring and monitoring the exact volume and momentary, instantaneous flow rate of urine produced by an individual during a urination session. The design of the present invention ensures that the following principles are kept:
1. Dynamic range: The apparatus accommodates the full dynamic range of expected urinary flow and volume; from single droplets to a strong flow of urine.
2. Sensitivity:
    a. There is no restriction of urine along the flow path en-route the measurement apparatus.
    b. Residual urine does not linger along the path of urine flow, or within the measurement apparatus, and does not diminish the accuracy of measurements.
    c. According to some embodiments, the apparatus is configured to specifically enhance the measurement accuracy of weak urine flow.
3. Instantaneous: The detection of momentary urinary flow rate (as opposed to estimation of average urinary flow through volume measurement), is essential in order to express the different properties of the flow. Such properties (e.g. fluctuations in the flow) are indicative of medical conditions, and may assist physicians in their diagnosis.
4. Uniformity: All measurements of urine flow are conducted in relation to a common physical baseline so as to eliminate the effect of artifacts that disrupt measurement uniformity among different patients. Such artifacts include a. Gender of patients
b. Height of urine disposal
c. Angle of urine disposal, etc.
5. Repetitiveness: Due to the design of the present invention, the apparatus may be independently employed by individual patients (e.g. in the comfort of their homes), and yet maintain the uniformity in measurements for the same patient. This information will indicate to physicians whether the patient's condition has changed over time.
6. Ease of use: In order to facilitate the principles of uniformity and repetitiveness, the present invention incorporates in its design important aspects of user-friendliness, e.g.: Easy assembly over a toilet bowl, hygienic rinse of the apparatus following every use, and automatic collection and transmission of the data for analysis.

FIG. 1 presents a section view of the flow meter apparatus, including a receptacle bowl 100, an encasement 200, divided to an upper part 200a and a lower part 200b, a fluid guide 600 and an impeller 400, and presents the flow of urine according to some embodiments of the present invention. The fluid flow path is indicated in a dashed line 1000.

The apparatus is configured to be placed over a toilet seat or toilet bowl, and direct urine onto an impeller, serving as a mechanical sensing device. According to these embodiments, the apparatus comprises at least part of:
  an encasement 200, configured to encase components of said apparatus.
  a receptacle bowl 100 attached to said encasement 200, configured to be placed over a toilet seat or toilet bowl, collect fluid during urination and direct said fluid through a single point of exit 110 to a fluid flow guide. According to some embodiments, the said receptacle bowl 100 further comprises at least one flap for placing the receptacle bowl 100 over a toilet bowl or a toilet seat;
  A fluid flow guide 600, configured to convey said fluid from the receptacle bowl 100 to the impeller 400;
  An impeller 400 configured to receive the flow of fluid from the flow guide 600, and rotate in a speed that is indicative of the fluid flow rate. According to some embodiments, the impeller 400 is mounted on a shaft 410, and is free to rotate along a rotation axis. According to some embodiments, the shaft is statically fixed within the encasement 200, and the impeller is mounted onto the shaft via a low friction hub and/or bearing, and is thus free to rotate over the shaft 410 along a rotation axis. According to some embodiments, the shaft is installed within the encasement 200 via at least one low friction hub and/or bearing, and the impeller 400 is fixed onto the shaft, thus both the impeller 400 and shaft 410 are free to rotate together along a rotation axis. According to some embodiments, the impeller 400 is installed within the encasement via at least one bearing or low friction hub 411, and is free to rotate by means of the said bearing(s) or low friction hub(s) along a rotation axis without the use of a shaft 410.
  a plurality of blades 420 attached to the impeller 400, configured to receive fluid from the flow guide 600 and rotate the impeller 400 at a speed that correlates with the flow rate of fluid;
  an angular velocity sensor 500, configured to produce electric signals that correlate with the angular velocity and/or angular position of the impeller 400;
  an electronic circuit 510, configured receive said electric signals, record them, save them, and optionally transmit the electric signals or derivatives thereof, by wired or wireless communication to a different location for further analysis; and According to some embodiments, the electronic circuit 510 is associated with a computerized system, configured to analyze said electric signals, to determine the momentary, instantaneous rotational speed of the impeller during urination, and analyze said determined momentary rotational speed of the impeller to extract the momentary, instantaneous rate of urine flow during urination.

The flow guide 600 is comprised of a set of enclosed fluid paths, configured to transfer fluid from the receptacle bowl 100 to the impeller 400. The said set of enclosed fluid guide paths may, or may not be integral to the encasement 200. The flow guide 600 comprises an inlet 110, configured to enable ingress of fluid from the receptacle bowl 100 to the flow guide 600, and an outlet 310, configured to enable egress of fluid from the flow guide 600 onto the impeller 400. The flow guide 600 is inclined in two planes, to provide free draining of fluid from said inlet 110 to said outlet 310 and onto the impeller 400, and the said inclination is configured to cause fluid droplets to overcome the retaining force of fluid surface tension and be directed towards the impeller 400 with minimal delay.

According to the embodiment depicted in FIG. 1, the apparatus' encasement 200 is comprised of two parts: an upper encasement 200a and a lower encasement 200b. In this embodiment, the flow guide 600 is integral to the said encasements.

The upper encasement 200a guides the flow of fluid, regardless of its initial velocity or direction to a single point of exit 110. The flow of urine is broken so as to cancel the effect of height of urine disposal into the receptacle bowl 100 on the urine velocity.

According to some embodiments, the lower encasement 200a is inclined in two planes, such that the urine flow is directed to a single outlet location 310. This inclination is configured so as to cause weak urine flow (e.g. <5 ml/second) and urine droplets to overcome the retaining force of fluid surface tension, and be directed to the single outlet location 310. A more elaborate description of the said upper encasement 200a and a lower encasement 200b is provided in relation to FIG. 4, below.

According to some embodiments of the present invention, the angular velocity sensor 500 comprises a stationary Hall effect sensor 500a. According to these embodiments:
  The impeller 400 comprises a plurality of permanent magnets 470a, located radially on its distal end (refer also to FIGS. 16a, 18a);
  The impeller 400 is installed in close proximity to said stationary Hall effect sensor 500a;
  The impeller 400 induces an electromagnetic signal due to full or partial rotation of the impeller wheel and the said incorporated plurality of permanent magnets 470a;
  said Hall effect sensor 500a is configured to sense the said electromagnetic signal induced by the proximate passage of said permanent magnets 470a in front of the Hall effect sensor 500a during said rotation of the impeller;
  The Hall effect sensor 500a produces electric signals that correlate with the angular velocity of the impeller 400. These electric signals are analyzed by a processor of a computerized system, to determine the instantaneous, momentary flow rate of urine, as explained further below.

The permanent magnets 470*a* may or may not:
be mounted in a common magnetic flux orientation, or
have the same magnetic field strength, either due to manufacturing tolerances of components or by design, or
be mounted with an equal rotational spacing.

According to some embodiments of the present invention, the said angular velocity sensor comprises a stationary photodiode sensor 500*b*. In these embodiments:
The impeller is installed in close proximity to said stationary photodiode sensor 500*b*;
The impeller comprises a plurality of LED 470*b* light sources, installed radially on the impeller's distal end (refer also to FIGS. 16*a*, 18*a*);
The stationary photodiode sensor 500*b* is configured to sense the light emitted from said LEDs 470*b* during proximate passage of the LEDs 470*b* in front of the photodiode sensor 500*b* during rotation of the impeller, and produce electric signals that correlate with the angular velocity of the impeller 400. These electric signals are analyzed by a computerized system, to determine the momentary flow rate of urine, as explained further below.

According to some embodiments of the present invention, the said angular velocity sensor comprises a rotary encoder 500*c* (please refer also to FIG. 14*a*). In these embodiments:
The shaft 410 is installed within the apparatus' encasement via a low friction hub and/or bearing, and is free to rotate along a rotation axis. The impeller 400 is fixed on the shaft, and is free to rotate with the shaft along the shaft's rotation axis;
The rotary encoder 500*c* is mounted on the shaft 410, and is configured to produce electric signals that correlate with the angular position and/or angular velocity of the shaft 410 during said rotation of the impeller 400 and shaft 410. These electric signals are analyzed by a computerized system, to determine the momentary flow rate of urine, as explained further below.

The apparatus further comprises an electronic circuit (not shown in FIG. 1), configured to receive the produced electric signals (either directly or following additional electronic transformations), and either analyze the electronic signals on board, or propagate them to be analyzed elsewhere. According to some embodiments, the electronic circuit is configured to:
analyze said electric signals, to determine the momentary rotational speed of the impeller during urination; and
analyze said determined momentary rotational speed of the impeller to extract the momentary rate of fluid flow during urination.

According to some embodiments, the said electronic circuit is configured to:
receive said produced electric signals;
propagate the electric signals or derivations thereof to a computerized system, via wired or wireless communication; and
the said computerized system is configured to analyze the said electric signals or derivations thereof, to determine the momentary rotational speed of the impeller during urination, and analyze the determined momentary rotational speed of the impeller to extract the momentary rate of fluid flow during urination.

According to one embodiment of the present invention, the analog electronic signal is converted by the electronic circuit to an audio stream, and is streamed through the microphone inlet of a Smartphone, upon which it is transformed to a digital electronic signal. This digital signal is then processed by a dedicated application on the Smartphone in real time, or is sent elsewhere for further processing.

FIG. 2 shows an elevated perspective view of the receptacle bowl 100, according to some embodiments of the present invention. The bowl comprises at least one flap 120 for placing the apparatus over a toilet bowl or a toilet seat. The fluid is directed via a single point of exit 110 to the upper encasement 200, and therefrom via the upper encasement's 200 single point of exit 210 to the lower encasement (not shown). The fluid flow path is indicated with a dashed arrow line 1000.

FIGS. 3 and 4 respectively present an elevated view and a frontal view of the receptacle bowl 100, according to additional embodiments of the present invention.

The receptacle bowl 100 comprises radial ribs 130, configured to prevent fluid from flowing around the receptacle bowl 100, reduce the flow momentum of the urine, and direct the fluid towards said single point of exit 110 in the bowl with minimal delay.

According to some embodiments, the receptacle bowl 100 further comprises concentric steps 140, configured to prevent fluid from flowing upwards along the sides of the receptacle bowl 100, and direct fluid towards the single point of exit 110 in the bowl with minimal delay.

According to some embodiments, the said concentric steps 140 are integrated within the said radial ribs 130 of the receptacle bowl 100, and within the gaps between the ribs 130.

FIG. 5 presents an exploded perspective view of the apparatus' encasement, distinguishing between an upper encasement part 200 and a lower encasement part 300, according to some embodiments of the present invention, and indicating the assembly of the two parts.

FIG. 6 shows a front section view of the assembled upper and lower encasement parts (200, 300 respectively) of an embodiment of the present invention, illustrating the fluid guide path 1000 with a dashed arrow line.

The urine that has been disposed of into the toilet receptacle bowl 100 arrives via the upper encasement's single exit point 210 to the lower encasement's fluid guide path 600. The influx of urine is broken at the fluid guide path 600, to absorb fluid momentum, and eliminate differences in urine velocity due to different height and orientation of urine disposal.

The lower encasement's 200*b* fluid guide path 600 is inclined in two planes, such that the urine flow is directed to a single outlet location 310.

The said inclination is sufficient for weak urine flow (e.g. <5 ml/s) and urine droplets to overcome the retaining force of fluid surface tension, and also be directed to the said single outlet location 310.

The fluid is therefrom guided to the impeller 400, where it is caught by the plurality of blades 420 incorporated within the impeller, causing the impeller to rotate in a velocity that corresponds with the urine's flow rate.

FIGS. 7*a* and 7*b* respectively show distal and proximal lateral section views of the flow meter assembly of the present invention, illustrating the fluid path from the fluid flow guide 600 onto the impeller 400, and therefrom to be flushed in the toilet according to some embodiments of the present invention.

The location of the said outlet 310 is in close proximity to the impeller, and transfer of individual droplets from the flow guide 600 to the impeller is promoted by the formation of a drop at the said single outlet location 310 of the flow guide, such that:

the gap 315 between the flow guide and the impeller is configured so that the fluid droplet, during its formation, contacts the impeller and flows onto the impeller, and is hence captured by the impeller at the earliest opportunity; and said gap is configured so as to ensure that the surface tension of the fluid cannot cause fluid droplets to affix to both the impeller and flow guide at the same time due to surface tension According to the embodiment depicted in FIGS. 7a and 7b, the impeller 400 is mounted on a shaft 410, having its rotating axis inclined with respect to the ground horizontal plane, such that fluid captured by the blades 420 is promoted to flow axially along the impeller blade 420 toward the flanged end 460 of the impeller.

According to the embodiment depicted in FIGS. 7a and 7b, the angular velocity sensor 500 comprises a stationary Hall effect sensor 500a, and the impeller 400 comprises a plurality of permanent magnets, radially located on the back of the impeller's flanged face 460, at the impeller's distal end. The stationary Hall effect sensor 500a is installed in close proximity to the said permanent magnets 470a. The Hall effect sensor 500a is configured to sense the magnetic field induced by the proximate passage of the magnets 470a during the impeller's full or partial rotation, and consequently emit an electronic output signal.

According other embodiments, the angular velocity sensor 500 comprises a stationary photodiode 500b, and the impeller 400 comprises a plurality of LED light sources 470b, radially located on the back of the impeller's flanged face 460, at the impeller's distal end. The stationary photodiode 500b is installed in close proximity to the LED light sources 470b, and is configured to sense the light emitted from said LEDs during proximate passage of said LEDs 470b in front of the photodiode sensor 500b, and consequently emit an electronic output signal. The illustration of the stationary photodiode 500b embodiment is substantially identical to that of the Hall effect sensor 500a embodiment discussed above, and has been omitted for the purpose of brevity.

The said electronic output signal is consequently propagated to an electronic circuit 510 for further processing, as elaborated further below.

FIG. 8 presents a section view of the flow meter apparatus, including a bowl, an encasement, a fluid guide 600 comprising a reservoir 610, and an impeller according to some embodiments of the invention.

Fluid is received in the receptacle bowl 100, and is transferred via a single point of exit 110 in the bowl to a flow guide 600, comprising a reservoir 610. The fluid flows through an array of baffles 620, oriented vertically within the reservoir 610, and therefrom proceeds towards a cascade wall 630. The fluid spills over the cascade wall 630 in a laminar flow onto the impeller, thus rotating it in an angular velocity that corresponds to the urine's flow rate. As the impeller 400 rotates, the fluid subsequently evacuates the impeller 400 from its bottom side directly into the toilet, to be easily flushed away at the end of urination.

FIG. 9 presents an elevated isometric view of the reservoir 610 and cascade 630, which is incorporated within the flow guide 600 according to some embodiments of the present invention. The reservoir 610 is configured to capture a known volume of incoming fluid during an initial phase of urination, and fill up to a known height, before allowing the fluid to proceed towards the impeller 400.

According to some embodiments, the volume of the reservoir 610 is configured so as to limit the initial phase of a urination session, to be less than one second. As the expected range of urination flow rate spans from 5 ml/sec to 50 ml/sec, a reservoir having volume of 5 ml should normally be adequate to match this limitation. After the initial phase of urination has elapsed, the flow of incoming urine from the receptacle bowl 100 to the reservoir 610 will be identical to the flow of urine from the reservoir onto the impeller 400.

The reservoir comprises a plurality of vertically oriented baffles 620, arranged in an array within the reservoir 610. This array of baffles 620 serves multiple purposes:

The baffles absorb the kinetic energy of the fluid flowing through the reservoir, eliminating the effects of urine disposal height and orientation, and enabling the apparatus to measure urine flow as the momentary quantity of disposed urine.

The existence of bubbles in the inspected urine has a potentially disruptive effect on the accuracy of the fluid flow rate measurement, as bubbles acquire volume within the impeller 400. The baffles utilize the fluid tension produced by the fluid's contact with the baffles to extract air bubbles from the fluid.

The turbulence of fluid flowing over the impeller has a potentially disruptive effect on the accuracy of the fluid flow rate measurement. The baffles utilize the fluid tension produced by the fluid's contact with the baffles to laminate the flow, and prevent turbulence in the fluid.

The relative distance between adjacent baffles within the baffle array is configured so as to utilize the fluid tension produced by the fluid's contact with said baffles to extract air bubbles from the fluid and prevent turbulence in the fluid, but to also accommodate the expected range of fluid flow rates, and avoid a backup flow of fluid.

The reservoir is bordered by a vertical cascade wall 630 on one side, enabling fluid to flow over the cascade wall when the level of fluid in the reservoir 610 surpasses the height of the cascade wall 630.

The cascade wall is installed above one side of said impeller 400, so as to direct the flow of fluid over the cascade wall 630 onto the impeller blades 420 located at that side of the impeller 400, thus producing torque and rotating said impeller 400 (see FIG. 13).

Reference is now made to FIG. 10, presenting a front section view of the reservoir according to some embodiments of the present invention. The top surface of the cascade wall has a smooth, round cross section 630a, configured to produce a laminar flow of fluid over the cascade wall. The bottom side of the cascade wall 630 comprises a sharp lower edge 630b, configured to release the fluid in a laminar flow onto said impeller blades 420.

According to some embodiments, a physical restrictor wall 650 is installed in a substantially vertical plane, substantially parallel to that of the cascade wall 630, thus forming a vertical gap 670 between the cascade wall 630 restrictor wall 650. The vertical gap facilitates the flow of fluid therein, from the reservoir onto the impeller blades. The bottom side of said physical restrictor wall 650b comprises a sharp lower edge, configured to release the fluid in a laminar flow onto said impeller blades.

According to some embodiments, the reservoir 610 further comprises a drain aperture 640, located at the bottom side of the cascade wall. The drain aperture 640 is configured to enable evacuation of fluid from the reservoir onto the impeller blades 420 in a constant, known rate and in a constant, known position. According to a preferred embodiment, the rate of fluid evacuation through the drain aperture is configured in respect to the expected range of fluid flow rates, so as to enable filling the reservoir with fluid during the initial phase of urination. The drain aperture is configured to enable complete evacuation of fluid from the reservoir after the end of urination.

According to some embodiments, the flow guide 600 comprises a vent aperture 660, preferably located near the top of the restrictor wall 650, enabling air into the reservoir 610, in order to preventing a condition of low pressure induced by the flow of urine, and enable the urine to flow freely onto the impeller 400.

The flow guide 600 and its components (e.g. the reservoir 610, baffles 620, cascade wall, physical restriction wall 650, and vertical gap 670) are configured to accommodate the entire expected range of urine flow rate, i.e. between 5 ml/sec 50 ml/sec, and prohibit backlog of fluid, turbulence in the urine flow and detachment of the flow from the cascade wall even at top fluid flow rates (i.e.: 50 ml/sec).

FIG. 11 presents a lateral view of the reservoir and the cascade wall 630 according to some embodiments of the present invention.

A unique combination of the features of the cascade wall 630 and the impeller 400 enhances the sensitivity of the apparatus' measurement of weak urine flow rates, and improves the apparatus' dynamic range of measurement:

a) The height of the cascade wall 630 is angled 630*c* in respect to the horizontal plane, so as to guide a laminar flow of fluid over the cascade wall 630 at the proximal side 630*d* onto the proximal side of the impeller blades 420, and consistently dispense laminar flow of fluid over an increasingly longer portion of the cascade wall 630, and onto an increasingly longer portion of the impeller blades 420 as the flow of fluid is increased.

b) In addition, the impeller's rotation axis is inclined with respect to the horizontal plane, such that fluid captured by the blades is directed to flow axially along the impeller blade, from the impeller's proximal side towards the impeller's distal side, where it evacuates the impeller 400 towards the toilet drain (see FIG. 13). This causes fluid that has been dispensed onto the proximal side of the impeller to stay longer on the impeller blades 420, produce torque on the impeller for a longer period of time, and have more effect on the impeller's velocity, hence enhancing the apparatus' sensitivity to weak fluid flows.

According to some embodiments, the cascade wall 630 further comprises a groove at the location of the wall's top, proximal side 630*d*. This groove is configured to ensure that the flow of fluid over the cascade wall is initiated at the location of the groove 630*d* when the flow of fluid is weak, and thus further enhance the apparatus' measurement sensitivity to weak urine flow rates.

According to some embodiments, the cascade wall 630 further comprises a sharp lip, at the location of the wall's top, distal side 630*e*. This lip is configured to produce surface tension, which prevents the fluid from over flowing on the cascade wall's high flow side 630*e*, i.e. the distal side. This design maintains a consistent bias of the flow of urine in favor of the cascade wall's low flow side, i.e. the proximal side 630*d*. The said consistent bias contributes to ensure that weak fluid flow is always initiated at the cascade wall's proximal side 630*d*.

According to some embodiments, the reservoir further comprises a pair of side walls 680, limiting the passage of fluid over the cascade, and avoiding spillage of urine beyond the impeller blades 420.

FIG. 12 depicts a top view of the cascade wall 630 and its surroundings according to some embodiments of the present invention, and clearly presents:

the top edge of the cascade wall 630;
the physical restrictor wall 650;
the vertical gap 670 between the cascade wall 630 and the physical restrictor wall 650;
the groove, at the proximal side of the cascade wall 630*d*; and
the sharp lip, at the distal side of the cascade wall 630*e*.

FIG. 13 presents an elevated isometric view of the reservoir 610, which is incorporated within the flow guide 600 according to some embodiments of the present invention. The embodiment of FIG. 12 differs from that depicted in FIG. 9 in the volume of fluid contained by the reservoir 610:

In FIG. 9, fluid is accumulated during the initial urination phase, until the level of fluid reaches the minimal height of the cascade wall 630.

In FIG. 12, the minimal height of the cascade wall 630 above the reservoir's floor is nil, fluid is not accumulated in the reservoir prior to proceeding to the cascade wall 630 and to the impeller 400, and the drain 640 is rendered unnecessary.

The embodiment of FIG. 9 is characterized by an effective utilization of the merits of the baffles, i.e. laminating the fluid flow through the reservoir, and extracting air bubbles from it, thus producing accurate flow rate measurements. The embodiment of FIG. 12 is characterized by minimal latency, as it requires no initial urination phase, and produces measurements from the very beginning of the urination session. The merits of both embodiments may be combined in a third, intermediate embodiment during the manufacturing or installation of the apparatus, to satisfy specific accuracy and latency requirements.

FIG. 14*a* is a lateral section view of the apparatus, presenting the path of urine flow 1000, according to some embodiments of the present invention.

As explained above, urine is disposed of within a receptacle bowl 100 (not shown), and is directed via a single exit point 110 in the receptacle bowl 100 onto a flow guide 600, comprising the baffled 620 reservoir 610. The reservoir is confined by the cascade wall 630 on one side. The height of the cascade wall 630 is biased, so as to initiate the flow of urine from the reservoir via the proximal side 630*d* of the cascade wall 630. As the flow of urine increases, fluid is made able to pass over higher sections of the cascade wall 630, located towards the distal side of the cascade wall 630.

The fluid pours over the cascade wall 630 in a laminar flow, devoid of air bubbles onto the impeller 400, which is free to rotate along a rotation axis 400*a*. The rotation axis 400*a* is inclined in respect to the horizontal plane, such that the proximal end of the rotation axis is elevated in respect to the distal end.

According to one embodiment, the apparatus comprises a shaft 410 that is fixed to the encasement 200, and the impeller is mounted onto said fixed shaft 410 via at least one low friction hub 411*a* and/or bearing 411, and is free to rotate in respect to the shaft along the rotation axis 400*a*. According to another embodiment, the impeller is fixedly mounted onto a shaft 410, and the shaft 410 is connected to the apparatus' encasement 200 via at least one low friction hub and/or bearing 411, enabling the shaft and impeller to rotate together along the rotation axis 400*a*.

Reference is now made to FIG. 14*b*, depicting the installation of the impeller within the encasement 200 according to yet another embodiment of the present invention. In this embodiment, the impeller is installed within the apparatus' encasement 200 via at least one low friction hub or bearing 411, and is thus free to rotate along the rotation axis 400*a* without being mounted on a shaft.

The impeller 400 comprises a plurality of blades 420, the design of which is discussed in detail further below. The blades 420 are configured to capture the flow of urine therein, and retain it on the impeller, until the mass of the collected fluid exceeds the rotating friction of the impeller, and the impeller is made to rotate at a speed that correlates with the urine's flow rate.

In addition, the blades are configured to direct the flow of urine along the impeller blade, down a slope that is substantially parallel to the impeller's rotation axis, from the impeller's proximal side towards the impeller's distal side. This causes fluid that has been dispensed onto the proximal side of the impeller to stay longer on the impeller blades 420, produce more torque on the impeller, and have more effect on the impeller's velocity, thus enhancing the sensitivity of the apparatus' measurement of weak urine flow rates.

The distal end of the impeller is attached to a flange 460, limiting the flow of urine therefrom, and releasing the urine from the impeller to the toilet drain via dedicated apertures.

FIG. 15 is a front section view of the apparatus, presenting the path of urine flow onto the impeller, and therefrom to the toilet drain, according to some embodiments of the present invention.

FIGS. 16A and 16B respectively show a front view and a lateral section view of the impeller 400 according to some embodiments of the present invention.

In this embodiment, the impeller 400 is mounted on a shaft 410, said shaft for the purpose of allowing free spinning rotation of the impeller on the shaft where the shaft may be fixed or free to spin in the encasement.

According to some embodiments of the present invention, the impeller 400 is designed to share a minimal contact surface area with the shaft 410 about which it rotates, in order to minimize the impeller's 400 rotating friction. Such an implementation is achieved by using a two-piece impeller body, with narrow contact patches 480 at the outermost longitudinal extremities of the impeller assembly.

The impeller comprises a plurality of radially attached blades, which are angled back 430 with respect to the impeller's radius, towards the fluid flow guide 600. The said angle 430 creates a concavity 440 having a defined volume, enabling the impeller blades to capture fluid therein, and retain it on the impeller, until the mass of the collected fluid exceeds the rotating friction of the impeller, and the impeller is made to rotate.

The distance of said concavities in relation to the axis of the impeller's rotation is configured so that said known amount of fluid creates torque that overcomes retaining friction forces applied to the impeller, and rotate the impeller.

According to some embodiments, the central cylindrical hub portion of the impeller 450 is of a proportionally large diameter such that captured droplets of fluid are retained at a large radius relative to the axis of rotation. This property maximizes the torque derived from the mass of the captured droplets.

The impeller incorporates a continuous round flange 460, perpendicular to the impeller's rotation axis, attached at the impeller's distal end. According to a preferred embodiment, the diameter of the flange 460 is larger than the radial span of the blades. The smooth surface of the flange's face 460 is configured to promote the transition of fluid droplets from the semi-enclosed blade region to the flange's rim, thus minimizing the retention of droplets in the blade's region due to surface tension. The large diameter of the flange 460 is configured to promote the extraction of fluid from the impeller due to the centrifugal force produced by its rotation.

The flange's 460 cross-section at the rim is thin, and thus configured to minimize the adherence of droplets to the lowermost edge of the impeller due to surface tension.

According to some embodiments, the flange 460 incorporates a plurality of permanent magnets 470a or LED light sources 470b, located radially on the flange's distal side, and in close proximity to the angular velocity sensor 500. The angular velocity sensor 500 is configured to sense the passage of said permanent magnets 470a or LED light sources 470b in proximity to the angular velocity sensor 500, for the purpose of deducing the angular velocity of the impeller therefrom.

FIGS. 17a and 17b respectively present a front view and a section view of the impeller, according to additional embodiments of the present invention. The conical impeller 400 of this embodiment presents a trapezoid cross section, as opposed to the cylindrical impeller depicted in FIGS. 15a and 15b, which presents a rectangular cross section.

In addition, the impeller of the embodiment depicted in FIGS. 16a and 16b is mounted on a shaft 410 using at least one low friction hubs or bearings 411.

FIGS. 18a, 18b and 18c respectively present a lateral view, and two section views of the impeller, according to additional embodiments of the present invention.

The impeller is sealed by a cap 490 on its proximal end, configured to avoid having fluid spill therefrom directly to the toilet drain, and forcing the fluid to flow along the blades towards the impeller's distal end.

The flange is attached to the said blades in a perpendicular plane to the impeller's rotation axis, at the distal end of the impeller 400. Apertures 461 in the said attachments enable fluid to evacuate the blades 420 onto the surface of the flange 460, and proceed therefrom to the toilet's drain.

The flange 460 comprises vanes 465, dividing the face of the flange to sections, and configured to restrict the fluid from passing from one section to another, and direct the fluid in a radial direction, thus evacuating the fluid from the face of the flange towards the toilet's drain with minimal delay.

According to some embodiments, the impeller blades 420 are angled so as to form two distinctive regions: a concavity region 440 and an impact region 420b.

The concavity region is already explained in relation to FIGS. 15a and 15b, above: The angle 430 of the blades forms a concavity 440 having a defined volume, enabling the impeller blades to capture fluid therein, and the mass of the collected fluid exerts a moment force, causing the impeller to rotate.

The impact region is a portion of the blade's exterior surface, which serves as a receptacle for fluid that pours onto the impeller 400. The impact of fluid on the said impact region transfers a portion of the fluid's inertia onto the impeller, and causes the impeller to rotate.

The angle of the blades 430 may be utilized as a parameter in the process of manufacturing the apparatus, in order to trade off between the required qualities of the impeller 400, i.e. sensitivity of the apparatus to the incoming mass of fluid vs. the impact of fluid upon the impeller's blades.

FIG. 19a is a front section view of the encasement, presenting the torque exerted by different forces applied on the impeller, according to some embodiments of the present invention.

The impeller is made to rotate in an anti-clockwise direction by the force moment that is exerted by the incoming fluid F1. According to some embodiments, the impeller further comprises a friction cap 495, attached to the impeller in a plane that is perpendicular to the impeller's rotation axis.

The friction cap 495 is configured to apply a stopping force F2 on the impeller, in order to prevent the impeller's angular speed from overshooting due to momentary acceleration, and thus improve the apparatus' dynamic range of fluid flow rate measurement.

According to some embodiments, the apparatus further comprising a spring coil 497 and a beam 496, wherein:
- the spring coil 497 is attached to the apparatus' encasement 200 on one end and attached to the beam 496 on the other end;
- the spring coil 497 is configured to exert a constant force on said beam 496; and
- the beam 496 is configured to constantly brush against the friction cap 495 during the rotation of the impeller, thus producing a constant friction force on the friction cap as a result of said constant force exerted by the coil.

Unknown, weak stopping forces that are intrinsic to the design of the apparatus (e.g. internal system friction forces) may produce variations in the fluid flow rate results. According to some embodiments, the stopping force F2 may be configured to be large enough to overcome the effect of these intrinsic weak stopping forces, and eliminate their effect on the apparatus' accuracy and repetitiveness of urine flow measurement results.

According to some embodiments, the stopping force F2 may be constant, linearly correlated, or non-linearly correlated with the angular velocity of the friction cap 495, and may be calibrated as part of the process of the apparatus' manufacturing and assembly.

FIG. 19b is a front section view of the encasement, presenting the torque exerted by different forces applied on the impeller, according to some embodiments of the present invention. In the embodiment depicted in FIG. 19b, at least one clutch plate 498 is within the encasement, and is configured to apply a friction force upon the friction cap 495 to produce said stopping force.

According to additional embodiments, the stopping force F2 may be produced by other methods, as known to persons familiar with the art, For example, the impeller's shaft 410 may be connected to the encasement 200 via closed bearings, configured to apply friction force upon the shaft.

The electronic circuit 510 receives the electric signal emitted by the angular velocity sensor 500. According to some embodiments, the electronic circuit 510 applies various electronic processing actions on the received electric signal, including for example: sampling, filtering and amplifying the electric signal.

According to some embodiments, the electronic circuit 510 comprises a storage device whereupon the received electric signal is saved, either in its original form or derivations thereof following the said electronic processing actions. According to a preferred embodiment, the received electric signal is saved as a digital audio file.

According to some embodiments, the electronic circuit 510 comprises a processor, and a storage device on which are stored modules of instruction code executable by the processor, whereupon execution of the instruction code, causes the processor to perform the steps of:
- saving the received electric signals or derivations thereof as a digital file;
- analyzing the saved digital file, to determine the momentary rotational speed of the impeller during urination; and
- analyzing said determined momentary rotational speed of the impeller to extract the momentary rate of fluid flow during urination.

According to some embodiments, the electronic circuit 510 is configured to propagate the received electric signals or derivations thereof to a remote computerized system comprising a processor, via wired or wireless communication, as a data stream or as a data file. The said processor of the remote computerized system is configured to perform the steps of:
- saving the said propagated electric signals or derivations thereof as a digital file;
- analyzing the saved digital file, to determine the momentary rotational speed of the impeller during urination; and
- analyzing the said determined momentary rotational speed of the impeller to extract the momentary rate of fluid flow during urination.

Consider the following as an exemplary embodiment
- the electronic circuit 510 receives the electric signals emitted by the angular velocity sensor 500;
- the electronic circuit 510 is configured to transform the received signals to audio signals;
- the electronic circuit 510 comprises an audio plug, and is connected via an audio cable to the microphone input of a smartphone, thus propagating the audio signals as streaming data to the smartphone; and
- the smartphone executes an application configured to analyzing the incoming stream of audio data and extracting the momentary rate of urine flow throughout the urination session.

FIG. 20 presents a flow diagram, depicting the process of analyzing the signals emitted by the angular velocity sensor 500, according to one embodiment of the present invention. As explained above, according to some embodiments this analysis may be performed by a processor on the electronic circuit 510, whereas according to other embodiments, this analysis may be performed by a processor residing in a remote computational system, such as a smartphone.

The analysis process embodiment depicted herein 19 relates to angular velocity sensor 500 embodiments that are based on detection of proximate passage of LEDs 470b or permanent magnets 470a in front of the angular velocity sensor 500, as described above in relation to FIG. 15a.

The electronic signal emitted by the angular velocity sensor 500 is saved as a digital file, either in its original form or as derivations thereof following electronic processing actions (step 710).

A software algorithm extracts the chronological timestamps of the leading edge of the angular velocity sensor 500 output (step 720).

The timestamp of passage of each individual permanent magnet 470a or LED 470b is extracted in relation to the initial timestamp data, into multiple timestamp datasets (step 730).

The period of a full revolution is calculated per each individual permanent magnet 470a or LED device 470b, thus removing errors from the timestamp data that may be introduced by non-uniformity of physical qualities among the plurality of magnets or LEDs, such as LED light intensity or magnet strength, magnet polarity and magnet phase angle (step 740).

According to some embodiments of the present invention, a calibration curve (e.g. linear, polynomial or spline interpolation) converts the timestamps of pulses pertinent to individual LED or magnet passage to a calibrated, instantaneous flow rate, per each of the individual magnets or LEDs (step 750).

The computed speed of rotation is optionally averaged among the plurality of magnets or LEDs, to determine the mean instantaneous flow rate (step 760).

According to some embodiments, the instantaneous flow rate is integrated over time to produce the total volume of urination (step 770).

According to some embodiments, the said urine flow and urine volume data pertaining to individual urination sessions is analyzed to assess the probability of a medical condition, and assist a physician in the process of diagnosis (step 780).

According to some embodiments of the present invention, the said urine flow and urine volume data pertaining to an individual patient is accumulated (e.g. within a database) over multiple urination sessions, to evaluate the progression of a specific patient's condition over time (step 790).

The invention claimed is:

1. An apparatus for measuring flow rate of urine, comprising:
    an encasement, configured to encase components of said apparatus;
    a receptacle bowl attached to said encasement, configured to be placed over a toilet bowl or seat, and direct fluid through a single point of exit to a fluid flow guide;
    the fluid flow guide, configured to transfer the fluid from the receptacle bowl to an impeller;
    the impeller, configured to rotate along a rotation axis, wherein said impeller comprises a plurality of blades, configured to receive the urine from the flow guide, and thereby rotate the impeller at a speed correlating with the flow rate of the urine; and
    an angular velocity sensor, configured to produce electric signals that correlate with angular velocity or angular position of the impeller, wherein the angular velocity sensor comprises a rotary encoder mounted to a shaft, and configured to sense rotation of the shaft and responsively to the sensed rotation to produce the electrical signals.

2. The apparatus of claim 1, wherein the shaft is fixed onto the encasement, wherein the impeller is mounted onto said shaft via at least one low friction hub and/or bearing, and is free to rotate in respect to the shaft along the rotation axis.

3. The apparatus of claim 1, wherein the impeller is fixedly mounted on the shaft, and the shaft is connected to the encasement via at least one low friction hub and/or bearing, enabling the shaft and impeller to rotate together along the rotation axis.

4. The apparatus of claim 1, wherein the impeller is installed within the encasement via at least one low friction hub and/or bearing, and is free to rotate by said low friction hub and/or bearing along the rotation axis.

5. The apparatus of claim 1, wherein the impeller further comprises a plurality of permanent magnets, located radially on a distal end of the impeller, and wherein the angular velocity sensor comprises a stationary Hall Effect sensor, configured to sense an electromagnetic signal induced by proximate passage of said permanent magnets, during rotation of the impeller, to produce the electric signals.

6. The apparatus of claim 1, further comprising an electronic circuit configured to receive the electric signals from the angular velocity sensor and responsively to determine a momentary rate of urine flow.

7. The apparatus of claim 1, further comprising: an electronic circuit configured to receive the electric signals from the angular velocity sensor, and to transmit the electric signals or derivations thereof by wireless or wired communication to a remote processor, configured to determine a momentary rate of urine flow during urination.

8. The apparatus of claim 1, wherein said receptacle bowl comprises radial ribs, configured to reduce flow momentum of the urine, prevent the fluid from flowing around the receptacle bowl, and direct the fluid towards the bowl's single point of exit with minimal delay.

9. The apparatus of claim 1 further comprising a friction cap, attached to the impeller, in a plane that is perpendicular to the rotation axis of the impeller.

10. The apparatus of claim 9, further comprising a spring coil and a beam, wherein:
    said spring coil is attached to the encasement on one end and attached to said beam on other end;
    said spring coil is configured to exert a constant force on said beam; and
    said beam is configured to constantly brush against said friction cap during rotation of the impeller to produce a friction force on the friction cap as a result of said constant force exerted by the coil.

11. The apparatus of claim 9, further comprising at least one clutch plate, installed within the encasement, and is configured to apply a friction force upon the friction cap to produce a stopping force.

12. An apparatus for measuring flow rate of urine, comprising:
    an encasement, configured to encase components of said apparatus;
    a receptacle bowl attached to said encasement, configured to be placed over a toilet bowl or seat, and direct fluid through a single point of exit to a fluid flow guide;
    the fluid flow guide, configured to transfer the fluid from the receptacle bowl to an impeller;
    the impeller, configured to rotate along a rotation axis, wherein said impeller comprises a plurality of blades, configured to receive the urine from the flow guide, and thereby rotate the impeller at a speed correlating with the flow rate of the urine; and
    an angular velocity sensor, configured to produce electric signals that correlate with angular velocity or angular position of the impeller;
    wherein said impeller further comprises a plurality of light emitting diode (LED) light sources, located radially on a distal end of the impeller, and wherein the angular velocity sensor comprises a stationary photodiode sensor, configured to sense light emitted from said LEDs during proximate passage of said LEDs during rotation of the impeller, to produce the electrical signals.

13. An apparatus for measuring flow rate of urine, comprising:
    an encasement, configured to encase components of said apparatus;
    a receptacle bowl attached to said encasement, configured to be placed over a toilet bowl or seat, and direct fluid through a single point of exit to a fluid flow guide;
    the fluid flow guide, configured to transfer the fluid from the receptacle bowl to an impeller;
    the impeller, configured to rotate along a rotation axis, wherein said impeller comprises a plurality of blades, configured to receive the urine from the flow guide, and thereby rotate the impeller at a speed correlating with the flow rate of the urine; and
    an angular velocity sensor, configured to produce electric signals that correlate with angular velocity or angular position of the impeller;
    wherein said receptacle bowl further comprises concentric steps, configured to prevent the fluid from flowing upwards, along sides of the bowl, and direct the fluid towards the bowl's single point of exit with minimal delay.

14. An apparatus for measuring flow rate of urine, comprising:
an encasement, configured to encase components of said apparatus;
a receptacle bowl attached to said encasement, configured to be placed over a toilet bowl or seat, and direct fluid through a single point of exit to a fluid flow guide;
the fluid flow guide, configured to transfer the fluid from the receptacle bowl to an impeller;
the impeller, configured to rotate along a rotation axis, wherein said impeller comprises a plurality of blades, configured to receive the urine from the flow guide, and thereby rotate the impeller at a speed correlating with the flow rate of the urine; and
an angular velocity sensor, configured to produce electric signals that correlate with angular velocity or angular position of the impeller;
wherein said blades are curved so as to create a concavity having a defined volume, enabling the impeller blades to capture fluid therein, and retaining the fluid on the impeller, until mass of the collected fluid exceeds rotating friction of the impeller, and the impeller is made to rotate.

15. The apparatus of claim 14, wherein a distance of said concavities in relation to the axis of rotation of the impeller is configured so that a known amount of fluid creates torque that overcomes retaining friction forces applied to the impeller, and rotates the impeller.

* * * * *